United States Patent
Bommarito

(10) Patent No.: US 9,839,712 B2
(45) Date of Patent: Dec. 12, 2017

(54) SYSTEMS AND METHODS FOR DETERMINING THE CLEANLINESS OF A SURFACE

(71) Applicant: 3M INNOVATIVE PROPERTIES COMPANY, St. Paul, MN (US)

(72) Inventor: G. Marco Bommarito, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 147 days.

(21) Appl. No.: 14/652,831

(22) PCT Filed: Oct. 29, 2013

(86) PCT No.: PCT/US2013/067175
§ 371 (c)(1),
(2) Date: Jun. 17, 2015

(87) PCT Pub. No.: WO2014/099131
PCT Pub. Date: Jun. 26, 2014

(65) Prior Publication Data
US 2015/0328351 A1    Nov. 19, 2015

Related U.S. Application Data

(60) Provisional application No. 61/783,340, filed on Mar. 14, 2013, provisional application No. 61/745,037, filed on Dec. 21, 2012.

(51) Int. Cl.
*G01N 21/47* (2006.01)
*A61L 2/28* (2006.01)
(Continued)

(52) U.S. Cl.
CPC ............ *A61L 2/28* (2013.01); *G01N 21/4738* (2013.01); *G01N 21/55* (2013.01); *G01N 21/94* (2013.01);
(Continued)

(58) Field of Classification Search
CPC ......... G01N 2021/551; G01N 21/4738; G01N 2201/061; G01N 21/94; G01N 21/55; A61L 2/28; B08B 13/00
See application file for complete search history.

(56) References Cited

U.S. PATENT DOCUMENTS 1,175,224 A    3/1916  Bleecker
2,461,011 A    2/1949  Taylor
(Continued)

FOREIGN PATENT DOCUMENTS

DE    19649925    6/1998
DE    19754717    7/1998
(Continued)

OTHER PUBLICATIONS

International Search Report for PCT International Application No. PCT/US2013/067175 dated Feb. 17, 2014, 4 pages.

*Primary Examiner* — Kara E Geisel
*Assistant Examiner* — Amanda Merlino

(57) ABSTRACT

Systems and methods for determining the cleanliness of a surface. Surface marking systems of the present disclosure can include a plurality of retroreflective microspheres dispersed in or dispensed on a carrier. Applicators of the present disclosure can include a container comprising the surface marking system, and a dispenser. Methods of the present disclosure can include applying the surface marking system to at least one discrete site on the surface; illuminating the at least one discrete site on the surface with visible light, after a cleaning; and detecting retroreflection emitted from
(Continued)

the at least one discrete site on the surface in response to illuminating the at least one discrete site to determine the effectiveness of the cleaning of the surface.

17 Claims, 12 Drawing Sheets

(51) Int. Cl.
    *G01N 21/55* (2014.01)
    *G01N 21/94* (2006.01)
    *B08B 13/00* (2006.01)

(52) U.S. Cl.
    CPC ........ *B08B 13/00* (2013.01); *G01N 2021/551* (2013.01); *G01N 2201/061* (2013.01)

(56) References Cited

U.S. PATENT DOCUMENTS

| | | |
|---|---|---|
| 2,726,161 A | 12/1955 | Beck |
| 2,842,446 A | 7/1958 | Beck |
| 2,853,393 A | 9/1958 | Beck |
| 2,870,030 A | 1/1959 | Stradley |
| 2,939,797 A | 6/1960 | Rindone |
| 2,965,921 A | 12/1960 | Bland |
| 2,992,122 A | 7/1961 | Beck |
| 3,468,681 A | 9/1969 | Jaupain |
| 3,946,130 A | 3/1976 | Tung |
| 4,192,576 A | 3/1980 | Tung |
| 4,312,676 A | 1/1982 | Hogseth |
| 4,367,919 A | 1/1983 | Tung |
| 4,564,556 A | 1/1986 | Lange |
| 4,758,469 A | 7/1988 | Lange |
| 4,772,511 A | 9/1988 | Wood |
| 4,931,414 A | 6/1990 | Wood |
| 6,285,359 B1 | 9/2001 | Ogasawara |
| 6,350,034 B1 * | 2/2002 | Fleming ................ G02B 5/124 359/529 |
| 7,718,395 B2 | 5/2010 | Carling |
| 7,780,453 B2 | 8/2010 | Carling |
| 7,785,109 B2 | 8/2010 | Carling |
| 8,084,410 B2 | 12/2011 | Carling |
| 2006/0223731 A1 | 10/2006 | Carling |
| 2009/0042757 A1 | 2/2009 | Carling |
| 2009/0248499 A1 | 10/2009 | Carling |
| 2009/0261270 A1 | 10/2009 | Carling |
| 2009/0276239 A1 | 11/2009 | Swart |
| 2012/0071376 A1 | 3/2012 | Carling |

FOREIGN PATENT DOCUMENTS

| | | |
|---|---|---|
| JP | 2000-112651 | 4/2000 |
| JP | 2000-347798 | 12/2000 |
| WO | WO 2007-057505 | 5/2007 |
| WO | WO 2008-088424 | 7/2008 |

* cited by examiner

SYSTEMS AND METHODS FOR DETERMINING THE CLEANLINESS OF A SURFACE

CROSS REFERENCE TO RELATED APPLICATIONS

This is a national stage filing under 35 U.S.C. §371 of PCT/US2013/067175, filed Oct. 29, 2013, which claims priority to U.S. Provisional Application Nos. 61/783,340, filed Mar. 14, 2013, and 61/745,037, filed Dec. 21, 2012, the disclosures of which are incorporated herein by reference in their entirety.

FIELD

The present disclosure generally relates to systems and methods for determining the cleanliness of a surface, and particularly, for determining the cleanliness of an environmental surface, e.g., in a healthcare environment, using a unique surface marking system. The present disclosure also relates to surface marking systems and applicators for applying such marking systems to a surface of interest.

BACKGROUND

In healthcare facilities, microorganisms may be released onto surfaces (e.g., solid surfaces, equipment surfaces, clothing, etc.) from infected individuals or otherwise. Once a surface becomes contaminated with microorganisms, contact with the contaminated surface may easily and readily transfer microorganisms to other locations, such as another surface, an individual, equipment, food, or the like. In addition, some of the patients of such facilities suffer from infections by pathogenic microbes and, thus, bring the pathogenic microbes into such facilities. Such microbial contamination and/or transfer can be particularly troublesome because many of those who are present in such facilities (e.g., patients) are sick and may be immunologically compromised. Such individuals therefore have an increased risk of becoming sick from infection by the contaminating microbes.

Contaminated surfaces in a hospital or healthcare setting have been found to contribute to the epidemic and endemic transmission of a variety of microorganisms or pathogens, including *Clostridium difficile*, vancomycin-resistant Enterococci (VRE), methycillin-resistent *Stapholococcus aureus* (MRSA), *Acinetobacter baumannii*, and *Psuedomonas aeruginosa*, as well as to the epidemic transmission of norovirus. Such pathogens have been associated with Healthcare Acquired Infections (HAIs). While environmental cleaning and disinfecting practices have become routine in such healthcare settings, there is still a need for a facile, structured, and robust monitoring system and method for monitoring an environment's cleanliness, and for monitoring the effectiveness of various cleaning and/or disinfecting procedures.

Some existing monitoring systems employ a UV dye marking system in a transparent carrier. The glow from the UV dye can only be observed using an appropriate black light, such that the dyes are invisible to environmental services (EVS) staff during the cleaning procedures. Typically, an EVS manager can apply the marking system to a number of surfaces in a patient room, an operating room, or the like, prior to cleaning. The surfaces that have been marked are unknown to the EVS cleaning staff. After cleaning, the EVS manager (e.g., shift manager) can return to the room with a black light to inspect the marked surfaces and establish whether the marking system was thoroughly removed from the surfaces of interest.

SUMMARY

The present inventor has determined that an integrated environmental hygiene monitoring solution includes the use of a visual marking system. The surface marking systems of the present disclosure can be semi-quantitative and are used to determine if a surface has been adequately physically cleaned. Such surfaces can include environmental surfaces (e.g., walls, equipment, furniture, etc.) or skin surfaces (e.g., in monitoring hand washing of healthcare staff). As such, the surface marking system can be a tool to measure the compliance of front-line environmental services (EVS) staff to various cleaning protocols. Visual inspection can be used to monitor the aesthetic appearance of a given environment. In addition, a useful and easy-to-use integrated monitoring solution for determining the cleanliness of an environment and/or for determining compliance with cleaning protocols can be important for EVS to properly manage cleaning a healthcare setting, such as a hospital.

Surface marking systems of the present disclosure can serve as a surrogate for an environmental soil. They can be designed to be covert. Surface marking systems of the present disclosure employ retroreflective microspheres, rather than a UV dye, and therefore do not require a specialized light source to determine cleaning results.

Some aspects of the present disclosure provide a method for determining the cleanliness of a surface. The method can include providing a surface marking system comprising a plurality of retroreflective microspheres dispersed in or dispensed on a carrier; applying the surface marking system to at least one discrete site on the surface; illuminating the at least one discrete site on the surface with visible light, after a cleaning; and detecting retroreflection emitted from the at least one discrete site on the surface in response to illuminating the at least one discrete site to determine the effectiveness of the cleaning of the surface.

Some aspects of the present disclosure provide an applicator for applying a surface marking system. The applicator can include a container defining a reservoir; a surface marking system positioned in the reservoir, the surface marking system comprising a plurality of retroreflective microspheres dispersed in or dispensed on a carrier; and a dispenser configured to dispense the surface marking system from the reservoir.

Other features and aspects of the present disclosure will become apparent by consideration of the detailed description and accompanying drawings.

DETAILED DESCRIPTION

Figure 1:
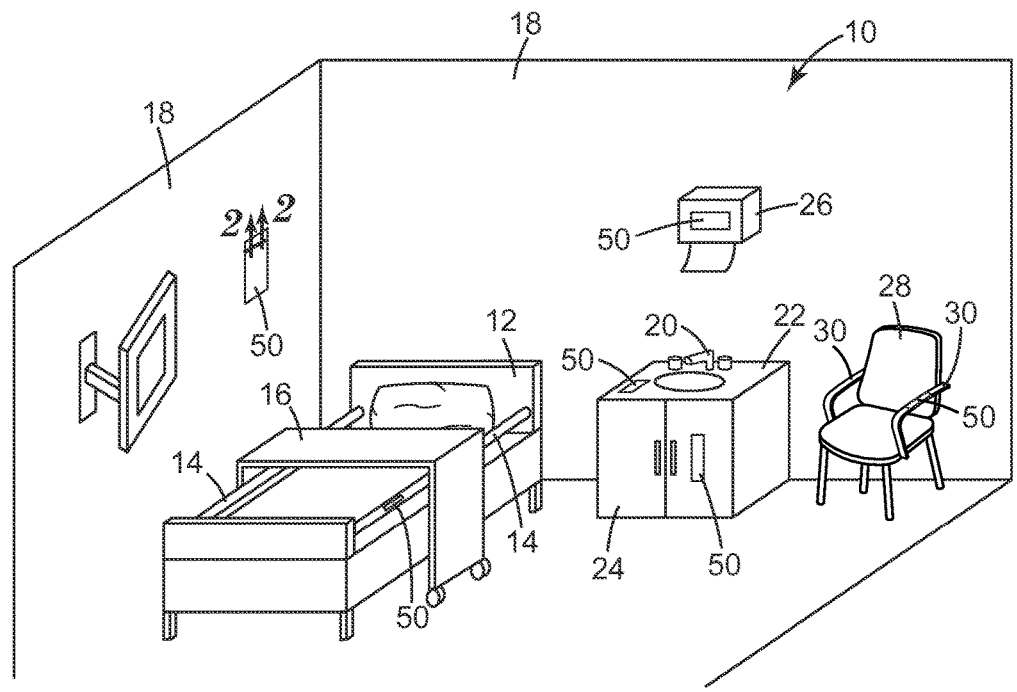
FIG. 1 illustrates a hospital room with a variety of environmental surfaces, and a plurality of discrete sites to which a surface marking system can be applied.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof is used broadly and encompasses both direct and indirect couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to visible-light-based surface marking systems, applicators for applying such surface marking systems to an environmental surface, and methods for determining the cleanliness of a surface and/or for determining compliance with cleaning protocols, e.g., by using such surface marking systems.

Methods of the present disclosure can include providing such surface marking systems comprising retroreflective microspheres; applying the surface marking system to a discrete site on a desired surface, allowing a cleaning procedure to take place; illuminating the same discrete site after cleaning with a visible light; and detecting the amount of retroreflection emitted from the same discrete site in response to the illumination to determine the effectiveness of the cleaning process based on the amount of retroreflection that is produced from the surface marking system remaining at the discrete site on the surface. Detection can be performed visually and/or automatically, e.g., with a device that can emit visible light and possibly capture retroreflectivity data, such as brightness, retroreflection, intensity, images that can later be analyzed using appropriate software, etc.

Retroreflective articles return incident light back towards the light source. Retroreflectivity in the present disclosure is provided by a plurality of transparent tiny beads or microspheres with a refractive index two times the refractive index of the medium from which the light source is incident. Under these conditions, the sphere surface behaves as a concave spherical mirror with the required curvature for retroreflection. However, the reflective index does not need to be twice that of the ambient medium to achieve retroreflection. Because the beads have a certain amount of spherical aberration, when the reflective index of the bead is at least 1.5 times that of ambient, there will be a radius from the centerline of the bead where a portion of the incident light is focused at the rear surface of the sphere giving rise to retroreflected light.

Retroreflectivity can also be provided in the present disclosure by a plurality of tiny beads or microspheres (e.g., made of glass) that cooperate with a reflective agent, such as a coated layer of aluminum. Such coatings can be partial coatings on the outer surfaces of the beads. Incident light entering an exposed portion of a bead (e.g., uncoated) is focused by the bead onto the reflective agent. The reflective agent reflects the incident light back through the bead, causing the light to exit through the exposed portion of the bead in a direction opposite the incident direction.

The microspheres (or "beads") of the present disclosure are substantially spherical in shape to provide uniform and efficient retroreflection. For example, the microspheres of the present disclosure are generally formed by being exposed to a spheroidization process, such as a melt-spheroidization process. The microspheres (i.e., uncoated portions) preferably also are highly transparent to minimize light absorption so that a large percentage of incident light is retroreflected. The microspheres often are substantially colorless but may be tinted or colored in some other fashion. The microspheres may be made from glass, a non-vitreous ceramic composition, or a synthetic resin. In general, glass and ceramic microspheres are preferred because they tend to be harder and more durable and tend to have more suitable indices of refraction than microspheres made from synthetic resins. Examples of microspheres that may be useful in this invention are disclosed in the following U.S. Pat. Nos. 1,175,224, 2,461,011, 2,726,161, 2,842,446, 2,853,393, 2,870,030, 2,939,797, 2,965,921, 2,992,122, 3,468,681, 3,946,130, 4,192,576, 4,367,919, 4,564,556, 4,758,469, 4,772,511, and 4,931,414. The disclosures of these patents are incorporated here by reference.

In some embodiments, the microspheres can have an average diameter of about 30 to 200 micrometers, in some embodiments, about 50 to 150 micrometers, and in some embodiments, about 10 to 100 micrometers. Microspheres smaller than the above ranges tend to provide lower levels of retroreflection, and microspheres larger than this range may impart an undesirably rough texture to the surface marking system. Microspheres used in the present disclosure can have a refractive index of about 1.5 to 3.0, in some embodiments, about 1.6 to 2.2, and in some embodiments, about 1.7 to 2.0.

In some embodiments, the microspheres can be coated with a specularly reflective material to enhance reflection. A variety of metals may be used to provide a specularly reflective metal layer. These include aluminum, silver, chromium, nickel, magnesium, gold, tin, nickel, tungsten, and the like, in elemental form.

Aluminum and silver are preferred metals for use in the reflective layer because they tend to provide good retroreflective brightness. In the case of aluminum, some of the metal may be in the form of the metal oxide and/or hydroxide.

The term "surface" or "environmental surface" generally refers to any surface present in a given environment. Examples of such surfaces that can be present in healthcare facilities (e.g., hospitals, doctor offices, nursing homes, etc.) can include, but are not limited to, walls (including doors), floors, ceilings, drains, ducts (e.g., airducts), vents, toilet seats, handles, doorknobs, handrails, bedrails (e.g., in a hospital), countertops, tabletops, eating surfaces (e.g., trays, dishes, etc.), working surfaces, equipment surfaces, clothing, etc., and combinations thereof. Examples of surfaces can also include skin surfaces, such as surfaces on hands.

As mentioned above, visible light can be used to detect surface marking systems of the present disclosure. For example, the surface marking system can work using the flash from a camera (which also be used to capture before cleaning and after cleaning images). Such a detection system can also be convenient in quantifying the results, because flash photography can be used to measure the amount of reflected light from the beads and thus establish if that surface was cleaned properly. The surface marking system can further include a carrier in or on which the retroreflective microspheres can be dispersed or dispensed in order to dispense the retroreflective microspheres onto a desired surface in a contact deposition mode or a non-contact deposition mode, e.g., using at least one of liquid deposition, spraying, and dry transfer methods.

One potential advantage for using visible light sources as opposed to specialized black light sources is that more convenient devices that may already be present in such a setting can be used for detection, as opposed to needing a specialized light source dedicated to the detection process that would not normally be present in that setting. Furthermore, when the visible light source is the flash of a camera or other flash-photography-capable device there is an inherent optimum geometry that maximizes the retroreflected light from the bead based marking system and minimizes variability in the measured intensity, since the flash and camera aperture/shutter are physically located in nearly the same plane and spatially separated by a very small distance. This is in contrast to using a physically separate black light source which is hand held by the user, and as such can be held in different locations and angles with respect to the detection system (generally the human observer), potentially giving rise to variability in the amount of viewable light emitted from the UV based marking system.

In addition, the surface marking systems of the present disclosure are particulate in nature. One advantage of using a particulate or particle-based surface marking system can be that effective removal of the surface marking system can only be accomplished by physical means. This is in contrast to a UV dye-based system where simple dissolution may suffice for removal. Since physical removal of contamination can be key to the disinfection process, the surface marking systems and methods of the present disclosure provide a more robust challenge for the cleaning process. Another potential advantage of using the particle-based surface marking system over a UV-dye-based system, is that the light emitted from the particle based system is point-like, and not a uniform glow as in the UV-dye-based systems, which can effectively provide a higher signal-to-noise ratio when measuring light output during detection. In addition, the point-like nature of the emitted light lends itself to analysis based on enumerating or counting the presence of discrete objects on the marked surface as a measurement of cleanliness. This is analogous to, for example, microbiological culture based methods where bacteria are enumerated on the surface of culture plates in order to quantify the concentration of a bacterial sample.

As mentioned above, the retroreflective microspheres can be suspended in, dispersed in and/or dispensed on a carrier. In embodiments in which the carrier is a solvent, the quick-drying carriers can be particularly useful. In embodiments in which the retroreflective microspheres are dispensed on the carrier, the carrier can be a thin layer of adhesive that will also require physical removal during the cleaning process. Generally, the carrier has two primary characteristics. First, the carrier does not significantly impede the cleaning process. That is, the carrier does not significantly increase the amount of time that one would need to wait prior to cleaning the marked room (e.g., quick-drying if the carrier is a liquid). Second, the carrier is generally designed to provide a challenge for removal that mimics an environmental soil (or skin soil) typical of the environment (or body part).

FIG. 1 illustrates an exemplary hospital room 10 comprising a bed 12 having bedrails 14, a tray 16, one or more walls 18, a sink 20, a countertop 22, a cupboard 24, a paper towel dispenser 26, and a chair 28 having an armrest 30. The above items shown in the hospital room 10 are shown by way of example only to demonstrate a variety of items having surfaces to be cleaned in a hospital cleaning protocol. Surfaces on these items can be marked using surface marking systems of the present disclosure, cleaned according to a cleaning protocol appropriate for the given environment, and monitored using the methods of the present disclosure. A variety of discrete marking sites 50 are shown in FIG. 1 that can be marked using surface marking systems of the present disclosure and monitored using methods of the present disclosure. For example, discrete sites 50 are shown on a bedrail 14, on a wall 18, on the countertop 22, on the cupboard 24, on the paper towel dispenser 26, and on the armrest 30 of the chair 28. While the discrete sites 50 are shown on surfaces in a hospital room, it should be understood that in some embodiments, the surface marking system 60 can be used to monitor hand hygiene and be used on skin as well.

Figure 2:
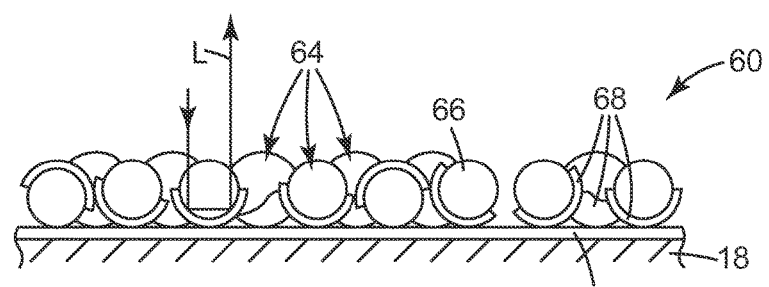
FIG. 2 is a close-up schematic cross-sectional view of a discrete site of FIG. 1 that has been marked with a surface marking system according to one embodiment of the present disclosure, taken along line 2-2 of FIG. 1.

FIG. 2 illustrates a surface marking system 60 according to one embodiment of the present disclosure. The surface marking system 60 includes a carrier 62, and a plurality of retroreflective microspheres 64 dispersed in or dispensed on the carrier 62.

As shown, the retroreflective microspheres 64 can include a base material 66 formed of any of the above-described materials or combinations thereof, and a coating 68, as described above. The coating 68 is illustrated as a partial coating over the base material 66 of each microsphere 64. The microspheres 64 may end up randomly oriented and distributed in or on the carrier 62, and ultimately, on the surface of interest. In such cases, at least enough of the microspheres 64 will end up oriented such that incident light can enter an exposed portion of a microspheres 64 and be reflected off the reflective coating 68 on the rear surface of the microsphere, back toward the light source, as illustrated by arrow L in FIG. 2.

The carrier 62 can be in a variety of forms and include a variety of materials. For example, in embodiments in which the microspheres 64 are dispensed in a liquid volumetric carrier 62, the carrier 62 can include, but is not limited to, one or more solvents that are at least as volatile as water at room temperature, e.g., 25 degrees C. (and in some embodiments, are more volatile than water at room temperature), one or more surfactants, one or more propellants (e.g., chlorofluorocarbons (CFCs), hydrofluoroalkanes (HFAs), etc.), one or more polymeric binders, or combinations thereof.

In some embodiments, the carrier 62 can include a non-solid phase that evaporates quickly (e.g., that is at least as volatile as water at room temperature, and in some embodiments, more volatile than water at room temperature), and if any solid components are present in the carrier 62, the solid components are water-soluble. Surface marking systems employing such carriers 62 would dry relatively quickly but would also be easily removed by standard cleaning (e.g., water-based) procedures and products, such that the surface marking system does not significantly impede cleaning procedures or present unnecessary cleaning challenges once dried onto a surface of interest.

Examples of solvents that are at least as volatile as water at room temperature that can be employed include, but are not limited to, water, alcohols (e.g., methanol, ethanol, propanol, isopropyl alcohol, etc.), acetone, methyl acetate, ethyl acetate, other suitable solvents that are at least as volatile as water at room temperature, or a combination thereof.

Examples of suitable surfactants can include, but are not limited to, anionic surfactants (e.g., dioctyl sodium sulfosuccinate, perfluorooctanesulfonate (PFOS), perfluorobutanesulfonate, linear alkylbenzene sulfonates), cationic surfactants (cetyl trimethylammonium bromide (CTAB) cetyl trimethylammonium chloride (CTAC) cetylpyridinium chloride (CPC), benzalkonium chloride (BAC), benzethonium chloride (BZT), 5-bromo-5-nitro-1,3-dioxane, dimethyldioctadecylammonium chloride, dioctadecyldimethylammonium bromide (DODAB), etc.); nonionic surfactants (e.g., polyoxyethylene glycol alkyl ethers, octaethylene glycol monododecyl ether, pentaethylene glycol monododecyl ether, polyoxypropylene glycol alkyl ethers, glucoside alkyl ethers, decyl glucoside, lauryl glucoside, octyl glucoside, polyoxyethylene glycol octylphenol ethers, polyoxyethylene glycol alkylphenol ethers, glycerol alkyl esters, polyoxyethylene glycol sorbitan alkyl esters: polysorbate, sorbitan alkyl esters, cocamide MEA, cocamide DEA, dodecyldimethylamine oxide, block copolymers of polyethylene glycol and polypropylene glycol, etc.); or combinations thereof.

In some embodiments, the retroreflective microspheres 64 can be randomly distributed in or on the carrier 62. In addition, in some embodiments, the carrier 62 can be water-soluble and can enable the surface marking system 60 to be temporary, removable with normal or typical cleaning procedures for a given environment or body surface, etc. In addition, in some embodiments, the surface marking system 60 is non-toxic, such that the retroreflective microspheres 64 and the carrier 62 are formed of non-toxic materials that do not present a hazard.

When the microspheres 64 are dispersed in a liquid volumetric carrier, the microspheres 64 can be dispersed in the carrier 62 at a concentration of at least about 1000 ($1\times10^3$) microspheres 64 per mL of carrier 62, in some embodiments, at a concentration of at least about 10,000 ($1\times10^4$), and in some embodiments, at a concentration of at least about 50,000 ($5\times10^4$). In some embodiments, the microspheres 64 can be dispersed in the carrier 62 at a concentration of no greater than about 1,000,000 ($1\times10^6$) microspheres 64 per mL of carrier 62, in some embodiments, at a concentration of no greater than about 500,000 ($5\times10^5$), and in some embodiments, at a concentration of no greater than about 100,000 ($1\times10^5$). In some embodiments, the microspheres 64 can be dispersed in the carrier 62 at a concentration ranging from 1000-1,000,000 microspheres 64 per mL of carrier 62.

In some embodiments, the carrier 62 can include an adhesive or an adhesive layer, and the microspheres 64 can be dispensed onto a surface of the adhesive, the adhesive being suitable for mimicking environmental (or skin) soil in a given environment (or body part). Such an adhesive can include, e.g., a double-side adhesive to adhere to a surface and hold the microspheres 64 in place on the surface sufficiently and reliably. In some embodiments, by way of example only, such an adhesive carrier can be dispensed from a tape dispenser that separates a release liner from the adhesive and lays the adhesive down on a surface while also dispensing the retroreflective microspheres on the adhesive. Adhesive carriers can include, but are not limited to, pressure sensitive adhesives including ones based on polyacrylates, natural rubber, synthetic rubber, spray adhesives, repositionable adhesives, and combinations thereof.

In embodiments employing an adhesive surface as the carrier 62, the microspheres 64 can be dispensed on the carrier 62 at a concentration of at least about 100 ($1\times10^2$) microspheres 64 per cm$^2$ of carrier 62, in some embodiments, at a concentration of at least about 1,000 ($1\times10^3$), and in some embodiments, at a concentration of at least about 5,000 ($5\times10^3$). In some embodiments, the microspheres 64 can be dispersed in the carrier 62 at a concentration of no greater than about 100,000 ($1\times10^5$) microspheres 64 per cm$^2$ of carrier 62, in some embodiments, at a concentration of no greater than about 50,000 ($5\times10^4$), and in some embodiments, at a concentration of no greater than about 10,000 ($1\times10^4$). In some embodiments, the microspheres 64 can be dispensed on the carrier 62 at a concentration ranging from 100-100,000 microspheres 64 per cm$^2$ of carrier 62.

One potential advantage of the surface marking systems employed in methods of the present disclosure is that the brightness and conspicuity of the surface marking systems of the present disclosure are superior to other existing marking systems. The Examples section below compares examples of surface marking systems of the present disclosure with a comparative microparticle system and existing UV-dye-based marking systems.

In some embodiments, in order to quantify and characterize the intensity or conspicuity of the surface marking system, a quality factor Q and a 'gain ratio' for the surface marking system can be obtained. As described in the Examples section below, for a given surface marking system, an intensity histogram can be created, e.g., which plots pixel frequency as the Y axis vs. pixel intensity as the X-axis. The intensity can also be approximated as representing a "lightness" value L present in a Lab color space with dimension L for lightness and "a" and "b" for the color-opponent dimensions, based on nonlinearly compressed CIE XYZ color space coordinates. The pixel frequency (or quantity) therefore provides the number of pixels with a given pixel intensity. Such pixel intensity histograms can then be curve-fit (e.g., as described in the Examples section), and three parameters can be extracted: $L_{MAX}$, $L_{FWHM}$, and $f_{Area}@L_{MAX}$. $L_{MAX}$ is the pixel intensity or "lightness" at the maximum normalized pixel frequency for the fit function. $f_{Area}@L_{MAX}$ is the normalized pixel frequency value corresponding to $L_{MAX}$. $L_{FWHM}$ is the pixel intensity full width at a normalized pixel frequency value that is exactly half of $f_{Area}@L_{MAX}$.

From these parameters, a quality factor $Q=L_{MAX}/L_{FWHM}$ can be calculated, for the non-illuminated state of the system ($Q_{Off}$) as well as for the illuminated state of the system ($Q_{On}$). The Q factors describe the distribution of pixel intensity across the entirety of the surface mark. High Q factors are representative of surface marks where there is a significant majority of pixels within a very narrow distribution (small $L_{FWHM}$) about a relatively high center intensity (large $L_{MAX}$). Low Q factors describe the opposite condition: surface marks where the significant majority of pixels have intensities spread out over a broad distribution (Large $L_{FWHM}$) centered about a relatively low intensity (small $L_{MAX}$). Furthermore, by calculating the ratio of $Q_{On}$ to $Q_{Off}$ (the 'gain ratio'), one can determine a quantity that is representative of the intensity gain for the system when it transitions from the non-illuminated to the illuminated state. This gain ratio describes the magnitude by which the surface mark becomes apparent to an observer when the illuminating source is turned on.

In some embodiments, the surface marking system 60 can be substantially invisible or at least inconspicuous (i.e., covert) to the EVS cleaning staff, and in some embodiments, the surface marking system 60 can be visible to the EVS cleaning staff.

In some embodiments, in order to quantify and characterize the visibility or covertness of the surface marking system, a transparency ratio for the surface marking system can be obtained. Using the Q factors described above, the ratio of $Q_{Off}$ to the Q factor determined for the non-marked and non-illuminated surface ($Q_{Background}$) is representative of the transparency of the surface mark on a given surface. This 'transparency ratio' is indicative of how "covert" the marked surface is to a given observer. Approaching a transparency ratio of 1.0 maximizes the covertness of the system.

Figure 3:
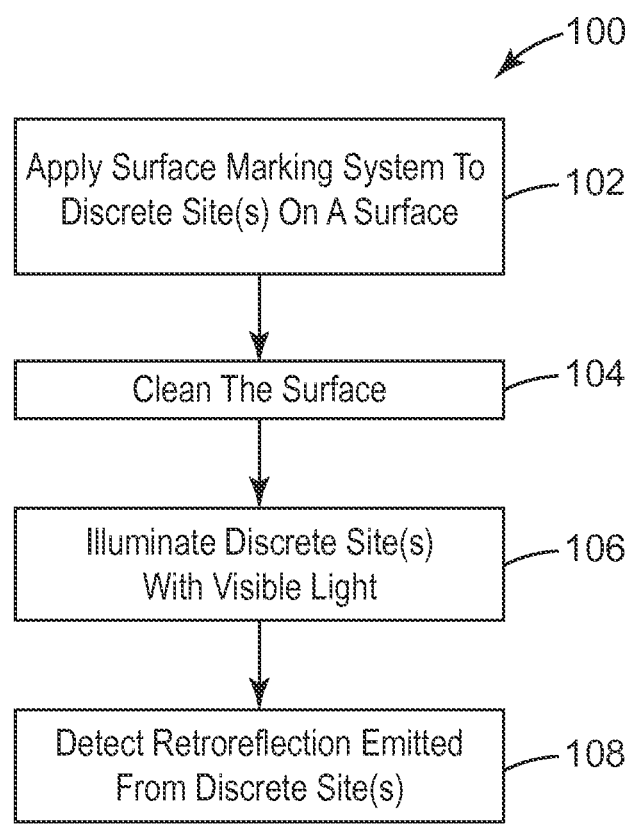
FIG. 3 is a flow chart describing a method of determining the cleanliness of a surface according to one embodiment of the present disclosure.
Figure 4:
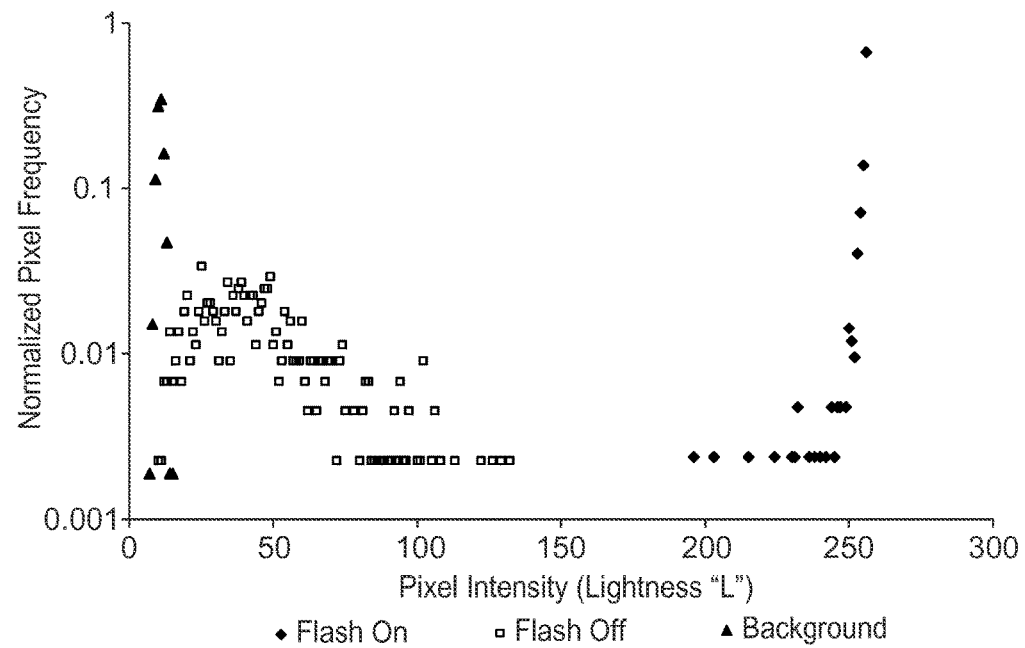
FIGS. 4-18 illustrate normalized pixel frequency versus pixel intensity for a variety of surface marking systems on a variety of surfaces, according to the Examples.
Figure 5:
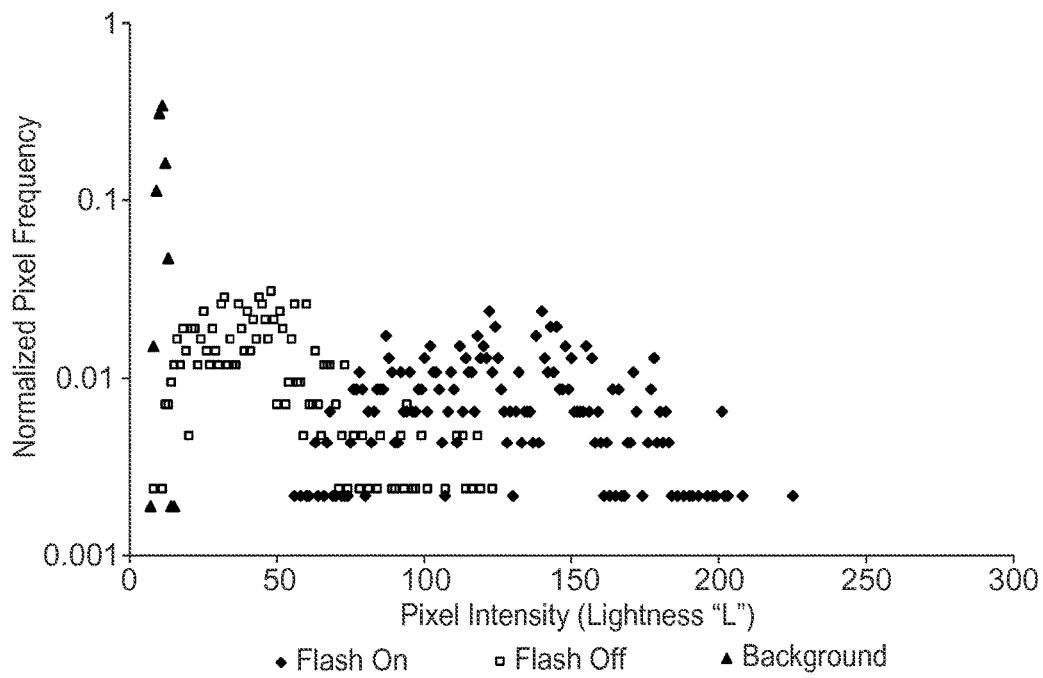
Figure 6:
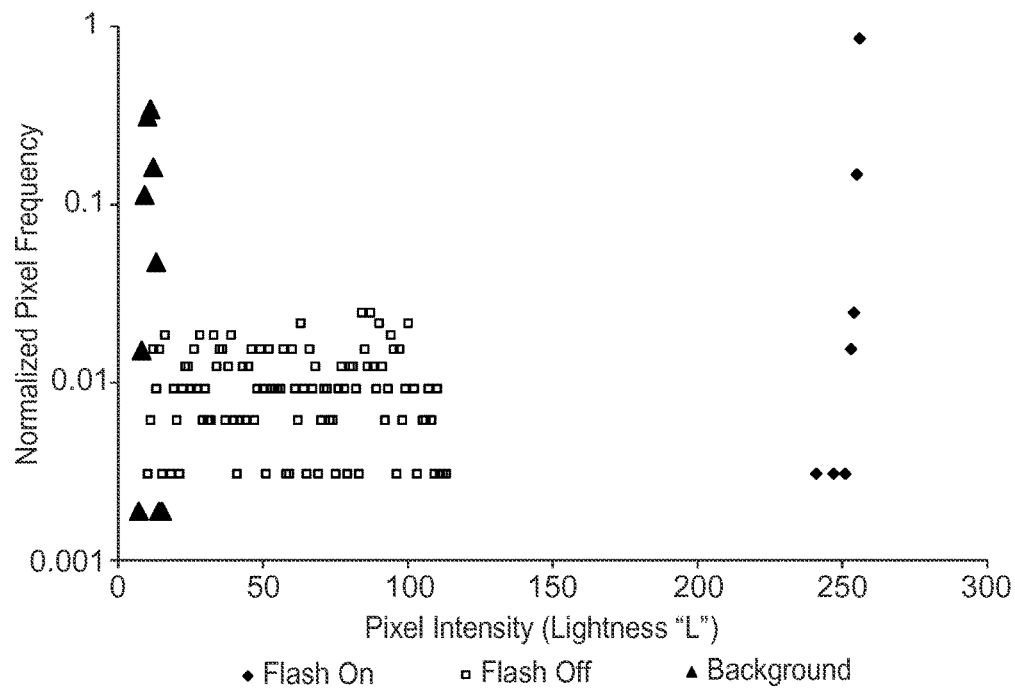
Figure 7:
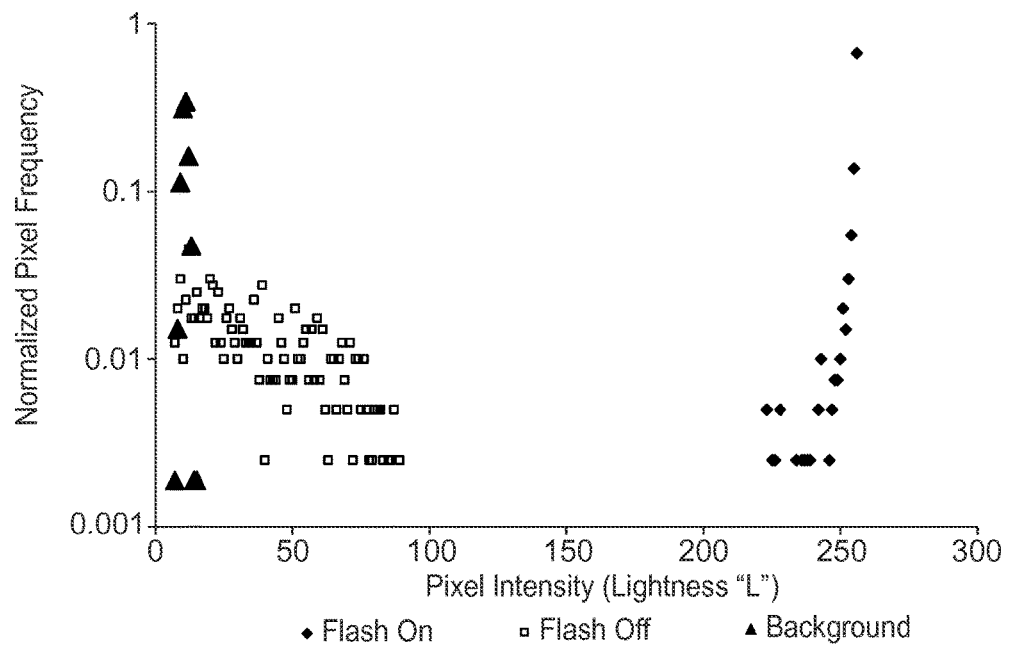
Figure 8:
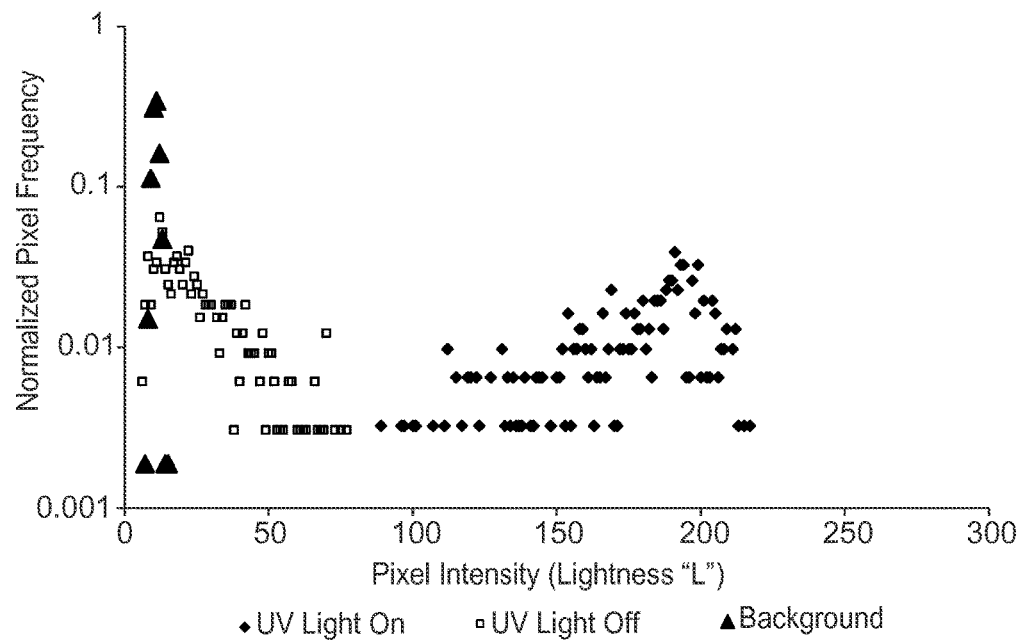

FIG. 3 illustrates a method 100 according to one embodiment of the present disclosure. As shown, the method 100 can include a first step 102 which includes applying a surface marking system to one or more discrete sites (e.g., the discrete sites 50 of FIG. 1) on a surface of interest. The method of application can be dependent on the type of surface marking system that is employed. For example, in embodiments employing a liquid carrier and retroreflective microspheres dispensed in the liquid carrier, at least one of liquid deposition (e.g., employing a roller ball), spraying, foaming, or the like, or combinations thereof, can be employed. Spraying and foaming can be examples of non-contact application modes, while liquid deposition can be an example of contact application modes. In some embodiments, non-contact application modes can be preferred to allow an applicator to be reused. Applicators employing contact methods of application may need to be re-sterilized or discarded after a single use.

As shown, the method 100 further includes a second step 104 of cleaning the surface. The second step 104 may not necessarily form a portion of the methods of the present disclosure, because the cleaning step may be performed by a different entity than the entity performing the remaining steps of the method 100. For example, as described above, in some embodiments, management may perform most of the steps of the method 100, and EVS cleaning staff may perform the cleaning step 104. In some embodiments in which the cleaning step 104 is performed by a separate entity than the remaining steps, the surface marking system can be covert, the discrete sites that have been marked with the surface marking system can be unknown to the cleaning entity (e.g., EVS staff), and/or the monitoring methods of the present disclosure may be unknown to the cleaning entity.

The method 100 further includes a third step 106 that includes illuminating the discrete sites that were marked in the first step 102 with a visible light. As mentioned above, a variety of light sources can be used to illuminate the discrete sites with visible light, including, but not limited to, at least one of a flashlight, a lamp, a lantern, a camera, a smart phone, a smart phone camera, a tablet computer, a tablet computer camera, other portable devices with integrated flash cameras, other suitable visible light sources, and a combination thereof.

The method 100 can further include a fourth step 108 which includes detecting emitted retroreflection from the discrete sites in response to illuminating the discrete sites. Based on the amount of retroreflected light that is emitted from each discrete site, the cleanliness of a surface can be determined and/or compliance with a cleaning protocol can be ascertained. As mentioned above, detection can be performed visually or with a detection device. A variety of detection devices can be employed with the methods of the present disclosure, including, but not limited to, at least one of a camera (e.g., any camera that is capable of flash photography; cameras used in conjunction with an external flash or a separate flashlight; etc.), other suitable detection devices, and combinations thereof.

Figure 21:
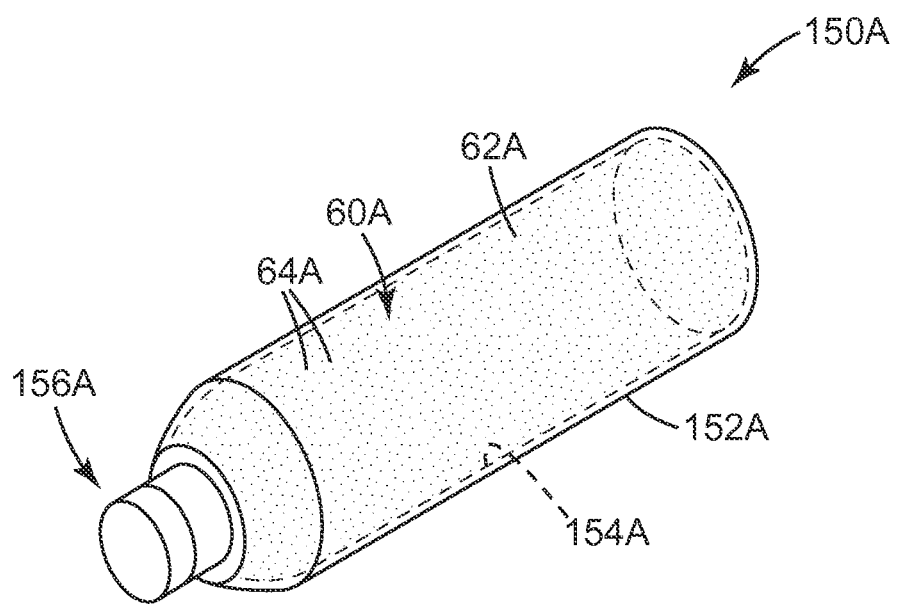
FIG. 21 is a perspective view of an applicator for a surface marking system according to one embodiment of the present disclosure.
Figure 22:
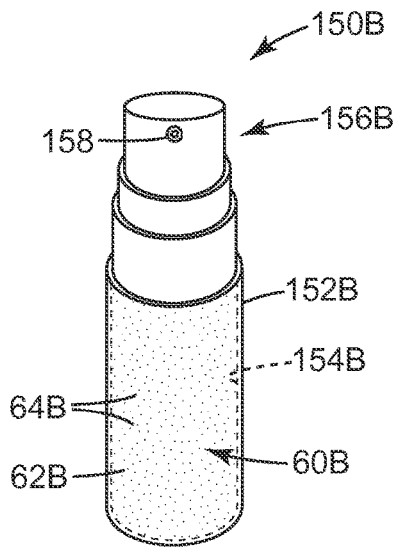
FIG. 22 is a perspective view of an applicator for a surface marking system according to another embodiment of the present disclosure.
Figure 23:
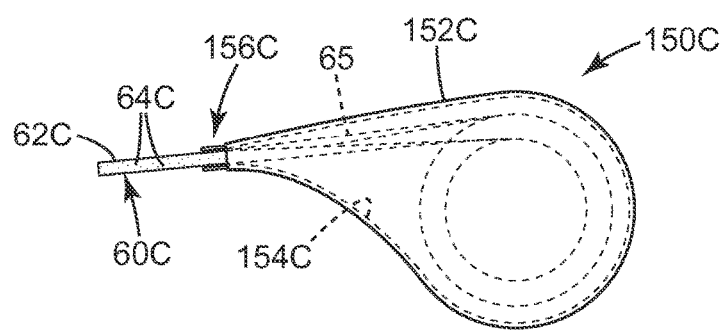
FIG. 23 is a perspective view of an applicator for a surface marking system according to another embodiment of the present disclosure.

FIGS. 21-23 illustrate exemplary applicators of the present disclosure. FIG. 21 illustrates an applicator 150A that can be used to spot, dab, paint, foam, or the like as means of applying a surface marking system to an environmental surface. The applicator 150A includes a container 152A that includes or defines a reservoir 154A configured to house a surface marking system 60A comprising retroreflective microspheres 64A dispersed in a carrier 62A (e.g., a liquid volumetric carrier). Any of the above-described liquid carriers and retroreflective microspheres can be employed. The applicator 150A further includes a dispenser or means for dispensing 156A configured to dispense the surface marking system 60A from the reservoir 154A (e.g., via the dispenser 156A). The dispenser 156A can be coupled to the container 152A and positioned in fluid communication with the reservoir 154A of the container 152A, such that the surface marking system 60A can be passed through the dispenser 156A to apply the surface marking system 60A to a surface. For example, in some embodiments, the sides of the container 152A can be squeezed to force the surface marking system 60A through the dispenser 156A. As mentioned above, the dispenser 156A can be configured to spot, dab, paint, foam, or the like, or combinations thereof, to apply the surface marking system 60A to a surface. As such, in some embodiments, the dispenser 156A can include a porous substrate that can be sized to pass the carrier 62A and the retroreflective microspheres 64A therethrough. For example, the dispenser 156A can include a sponge, a foam, a swab, a brush, a dabber, a filter membrane, a screen, or the like, or combinations thereof.

FIG. 22 illustrates an applicator 150B that can be used to spray, squirt, foam and/or atomize as means of applying a surface marking system to an environmental surface. The applicator 150B includes a container 152B that includes or defines a reservoir 154B configured to house a surface marking system 60B comprising retroreflective microspheres 64B dispersed in a carrier 62B (e.g., a liquid volumetric carrier). Any of the above-described liquid carriers and retroreflective microspheres can be employed. The applicator 150B further includes a dispenser or means for dispensing 156B configured to dispense the surface marking system 60B from the reservoir 154B. For example, in some embodiments, the dispenser 156B can include a nozzle 158 that is in fluid communication with the reservoir 154B. By way of example only, the nozzle 158 is shown as including a pump spray nozzle, but it should be understood that a variety of nozzles (e.g., aerosol, or the like) can instead be employed.

FIG. 23 illustrates an applicator 150C that can be used to apply a surface marking system to an environmental surface. The applicator 150C includes a container 152C that includes or defines a reservoir 154C configured to house a surface marking system 60C comprising retroreflective microspheres 64C dispensed on a carrier 62C (e.g., an adhesive layer). Any of the above-described adhesive or two-dimensional carriers and retroreflective microspheres can be employed. The applicator 150C further includes a dispenser or means for dispensing 156C configured to dispense the surface marking system 60C from the reservoir 154C. For example, such an adhesive carrier 62C can be dispensed from the applicator 150C, which is shown by way of example only as being a tape dispenser and means for separating a release liner (or backing) 165C from the adhesive carrier 62C, such that the applicator 150C lays the adhesive carrier 62C down on a desired surface. The retroreflective microspheres 64C can simultaneously be dispensed onto the adhesive carrier 62C, or the microspheres 64C can be dispensed on the adhesive carrier 62C prior to being loaded into the applicator 150C.

Figure 24:
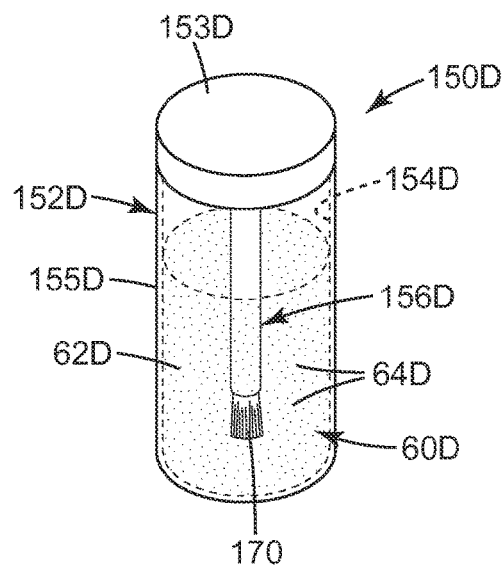
FIG. 24 is a perspective view of an applicator for a surface marking system according to another embodiment of the present disclosure.

FIG. 24 illustrates an applicator 150D that can be used to apply a surface marking system to an environmental surface. The applicator 150D includes a container 152D that includes or defines a reservoir 154D configured to house a surface marking system 60D comprising retroreflective microspheres 64D dispersed in a carrier 62D (e.g., a liquid volumetric carrier). Any of the above-described liquid carriers and retroreflective microspheres can be employed. The applicator 150D further includes a dispenser or means for dispensing 156D configured to transfer the surface marking system 60D from the reservoir 154D to a surface of interest. For example, in some embodiments, the container 152D can include a lid or cover 153D removably coupled to a base 155D, and the dispenser 156D can be coupled to the lid 153D, such that when the lid 153D is removed from the base 155D, the lid 153D can be grasped like a handle, and the surface marking system 60D can be applied to a surface of interest using the dispenser 156D. Other configurations and variations of the applicator 150D, and particularly the container 152D, are within the scope of the present disclosure. By way of example only, the dispenser 156D is shown as including a brush 170; however, it should be understood that in some embodiments, the dispenser 156D can include a sponge, a foam, a swab, a dabber, etc., or combinations thereof. In some embodiments, the dispenser 156D can include a porous substrate.

Each embodiment shown in FIGS. 21-24 is illustrated as a separate embodiment for clarity in illustrating a variety of features of the applicators of the present disclosure. However, it should be understood that any combination of elements and features of any of the embodiments illustrated in the figures and described herein can be employed in the applicators of the present disclosure.

The following embodiments are intended to be illustrative of the present disclosure and not limiting.

EMBODIMENTS

Embodiment 1 is a method for determining the cleanliness of a surface, the method comprising:
providing a surface marking system comprising a plurality of retroreflective microspheres dispersed in or dispensed on a carrier;
applying the surface marking system to at least one discrete site on the surface;
illuminating the at least one discrete site on the surface with visible light, after a cleaning; and
detecting retroreflection emitted from the at least one discrete site on the surface in response to illuminating the at least one discrete site to determine the effectiveness of the cleaning of the surface.

Embodiment 2 is the method of embodiment 1, wherein detecting includes visually detecting.

Embodiment 3 is the method of embodiment 1 or 2, wherein the surface is an environmental surface.

Embodiment 4 is the method of any of embodiments 1-3, wherein the at least one discrete site on the surface is unknown to environmental services staff.

Embodiment 5 is the method of any of embodiments 1-4, wherein the surface marking system is covert.

Embodiment 6 is the method of any of embodiments 1-5, wherein the plurality of retroreflective beads are randomly distributed in or on the carrier.

Embodiment 7 is the method of any of embodiments 1-6, wherein the surface marking system is comprised of non-toxic material.

Embodiment 8 is the method of any of embodiments 1-7, wherein the carrier is water-soluble.

Embodiment 9 is the method of any of embodiments 1-8, wherein applying the surface marking system includes non-contact application.

Embodiment 10 is the method of any of embodiments 1-9, wherein applying the surface marking system includes spraying.

Embodiment 11 is the method of any of embodiments 1-10, wherein applying the surface marking system includes foaming.

Embodiment 12 is the method of any of embodiments 1-11, wherein applying the surface marking system includes dry transfer.

Embodiment 13 is the method of any of embodiments 1-12, wherein applying the surface marking system includes contact application.

Embodiment 14 is the method of any of embodiments 1-13, wherein applying the surface marking system includes liquid deposition.

Embodiment 15 is the method of any of embodiments 1-14, wherein each of the plurality of retroreflective microspheres is at least partially coated with a reflective coating.

Embodiment 16 is the method of any of embodiments 1-15, wherein the plurality of retroreflective microspheres are dispersed in the carrier to a concentration of no greater than about $1 \times 10^6$ microspheres/mL of the carrier.

Embodiment 17 is the method of any of embodiments 1-16, wherein the plurality of retroreflective microspheres are dispersed on the carrier to a concentration of no greater than about $1 \times 10^5$ microspheres/cm$^2$ of the carrier.

Embodiment 18 is the method of any of embodiments 1-17, wherein the plurality of retroreflective microspheres includes an average diameter of 10 to 100 micrometers.

Embodiment 19 is the method of any of embodiments 1-18, wherein the carrier includes at least one of a surfactant, a polymeric binder, an adhesive layer, and a combination thereof.

The following working examples are intended to be illustrative of the present disclosure and not limiting.

Embodiment 20 is an applicator for applying a surface marking system, the applicator comprising:

a container defining a reservoir;

a surface marking system positioned in the reservoir, the surface marking system comprising a plurality of retroreflective microspheres dispersed in or dispensed on a carrier; and a dispenser configured to dispense the surface marking system from the reservoir.

Embodiment 21 is the applicator of embodiment 20, wherein the dispenser includes a porous substrate.

Embodiment 22 is the applicator of embodiment 20 or 21, wherein the dispenser includes at least one of a sponge, a foam, a swab, a brush, a dabber, or a combination thereof.

Embodiment 23 is the applicator of any of embodiments 20-22, wherein the dispenser includes a nozzle.

Embodiment 24 is the applicator of any of embodiments 20-23, wherein the carrier includes an adhesive, and wherein the container includes a tape dispenser.

Embodiment 25 is the applicator of any of embodiments 20-24, wherein the carrier includes a solvent that is at least as volatile as water at room temperature.

Embodiment 26 is the applicator of any of embodiments 20-25, wherein the carrier includes an alcohol.

EXAMPLES

Environmental Markers

Six different marker systems were evaluated—three Examples (Examples 1-3) of surface marking systems of the present disclosure employing visible-light-based systems and retroreflective microspheres, two Comparative Examples (C1 and C2) employing UV (fluorescent)-based marking systems, and one Comparative Example (C3) employing a visible-light-based system and microparticles (i.e., that were not formed into microspheres).

Example 1 was prepared with retroreflective microspheres, designated "W" beads, which were formed general glass recycle untreated microspheres with particle size less than 49 microns.

Example 2 was prepared with retroreflective microspheres, designated "Y" Beads, which were finished chromium treated microspheres with the following size distribution:

TABLE 1

Y Beads Particle Size Distribution

| % | Minimum | Maximum |
|---|---------|---------|
| 5% | 47 microns | 70 microns |
| 50% | 41 microns | 56 microns |
| 95% | 30 microns | 45 microns |

Example 3 was prepared with retroreflective microspheres designated "Z" beads, which were finished chromium treated microspheres with the size distribution detailed in Table 2.

Figure 19:
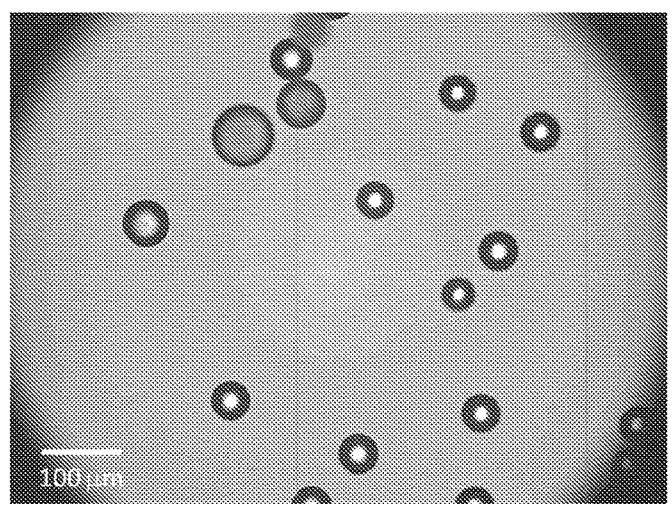
FIG. 19 is a photomicrograph of the retroreflective microspheres of Example 3, as described in the Examples section.

FIG. 19 is a photomicrograph of the Z beads, taken at 20×, with a digital color camera microscope: Leica DFC360 FX 11547002, available from Leica Microsystems CMS GmbH of Wetzlar, Germany

TABLE 2

Z Beads Particle Size Distribution

| % | Minimum | Maximum |
|---|---------|---------|
| 5% | 87 microns | 92 microns |
| 50% | 64 microns | 69 microns |
| 95% | 46 microns | 52 microns |

Comparative Example C1 was trade name GLO GERM, a white emulsion available from the Glo Germ Company of Moab, Utah as the product MINI GEL in a 2 ounce bottle (MG2O).

Comparative Example C2 was trade name DAZO Fluorescent Marking System available from Ecolab of St. Paul, Minn.

Comparative Example C3 was prepared with microparticles, which were milled glass recycle untreated unformed particles with particle size less than 49 microns.

Figure 20:
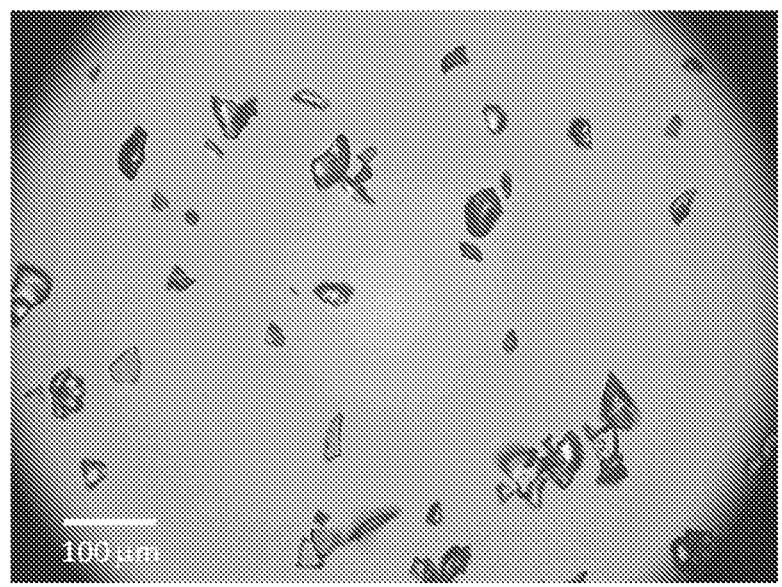
FIG. 20 is a photomicrograph of the microparticles of Comparative Example C3, as described in the Examples section.

FIG. 20 is a photomicrograph of the microparticles of Comparative Example C3, taken at 20×, with a digital color camera microscope: Leica DFC360 FX 11547002, available from Leica Microsystems CMS GmbH of Wetzlar, Germany.

Environmental Surfaces

Four different test surfaces were tested. Test Surface #1 was a black colored textured plastic. Test Surface #2 was a dark grey colored FORMICA brand surface. Test Surface #3 was a light grey colored FORMICA brand surface. Test Surface #4 was a finished (stained and varnished) natural cherry wood surface.

Sample Preparation

The UV markers (Comparative Examples C1-C2) were used "as is" according to manufacturer's instructions (shaken before used).

The retroreflective microspheres of Examples 1-3, and the microparticles of Comparative Example C3 were prepared as suspensions in isopropyl alcohol (IPA) at a concentration of 0.5 grams of microspheres/particles per 25 mL of IPA.

All the prepared Examples and Comparative Examples were transferred to a clean empty DAZO marking system container which had an approximately 2.2 cm circular (flat) stamp application (dauber) head. Therefore, all samples were applied to the test surfaces with the same type and size applicator, and shaken before used/applied.

Test Method

All the Examples were applied to the black Test Surface #1, and select examples were also applied to the other test surfaces #2, #3, and #4, using the dabber applicator described above, creating an approximately circular marker spot of about 2.5 centimeters in diameter. Digital photos were taken of the different markers on the different test surfaces at a constant distance of approximately 50 cm, using an APPLE iPhone4S, while keeping the orientation of the camera itself in a plane approximately parallel to the plane of the test surface being photographed. The reflective microspheres Examples 1-3 and the microparticles of Compartive Example C3, were photographed with the iPhone4S flash set to "ON" and separately with the flash set to "OFF." The fluorescent markers, Comparative Examples C1 (GLO GERM), and C2 (DAZO) were photographed with the flash "OFF" while under a UV light and with no UV light. Additionally, prior to marking the test surfaces, the surfaces were photographed with the flash "OFF" as a "background" measure.

Sample Data Processing

The digital photographs were transferred as jpg files into SigmaScan V5.0 (available from Systat Software Inc.) and then the surface area to be analyzed was selected to generate an intensity histogram using the software. The histograms were a plot of Pixel Frequency as the Y axis vs. Pixel Intensity as the X-axis, where the Intensity is a relative number between zero to 256. Where zero represents black or minimum lightness and 256 represents maximum white or maximum lightness. The Intensity can also be approximated as representing a "Lightness" value L present in a Lab color space with dimension L for lightness and "a" and "b" for the color-opponent dimensions, based on nonlinearly compressed CIE XYZ color space coordinates. The pixel frequency (or quantity) therefore provides the number of pixels with a given pixel intensity. The histograms were further processed by normalizing the pixel frequency values to a total of 1.0 for each graph, so that appropriate overlays of different photo data could be placed in the same histogram, such as the background measure, the flash "on" and the flash "off" photos. The same was done for the UV light on and UV light off photos. The normalized processed histograms are shown in FIGS. 4-16 for the various Examples and Comparative Examples on the different Test Surfaces.

TABLE 3

Example 1 (FIG. 4) & Comparative Example C3 (FIG. 5) on Test Surface #1 (Black)

| Parameter | Ex. 1 Flash On | Ex. 1 Flash Off | Ex. C3 Flash On | Ex. C3 Flash Off | Background Flash Off |
|---|---|---|---|---|---|
| Pixel Intensity at max frequency | 256 | 25 | 122 & 140 | 48 | 11 |
| Normalized Pixel Frequency at max Intensity | 0.664 | 0.034 | 0.024 | 0.031 | 0.344 |

TABLE 4

Example 2 (FIG. 6) & Example 3 (FIG. 7) on Test Surface #1 (Black)

| Parameter | Ex. 2 Flash On | Ex. 2 Flash Off | Ex. 3 Flash On | Ex. 3 Flash Off | Background Flash Off |
|---|---|---|---|---|---|
| Pixel Intensity at max frequency | 256 | 84 | 256 | 12 | 11 |
| Normalized Pixel Frequency at max Intensity | 0.858 | 0.025 | 0.668 | 0.045 | 0.344 |

TABLE 5

Comparative Example C1 (FIG. 8) & Comparative Example C2 (FIG. 9) on Test Surface #1 (Black)

| Parameter | Ex. C1 GLO GERM UV On | Ex. C1 GLO GERM UV Off | Ex. C2 DAZO UV On | Ex. C2 DAZO UV Off | Background Flash Off |
|---|---|---|---|---|---|
| Pixel Intensity at max frequency | 191 | 12 | 190 | 11 | 11 |
| Normalized Pixel Frequency at max Intensity | 0.039 | 0.065 | 0.072 | 0.312 | 0.344 |

TABLE 6

Example 3 (FIG. 10) and Comparative Example C1 (FIG. 11) on Test Surface #2 (Dark Grey)

| Parameter | Ex. 3 Flash On | Ex. 3 Flash Off | Ex. C1 GLO GERM UV On | Ex. C1 GLO GERM UV Off | Background Flash Off |
|---|---|---|---|---|---|
| Pixel Intensity at max frequency | 255 | 72 | 112 & 117 | 73 | 70 |
| Normalized Pixel Frequency at max Intensity | 0.446 | 0.025 | 0.014 | 0.047 | 0.074 |

TABLE 7

Example 3 (FIG. 12) and Comparative Example C1 (FIG. 13) on Test Surface #3 (Light Grey)

| Parameter | Ex. 3 Flash On | Ex. 3 Flash Off | Ex. C1 GLO GERM UV On | Ex. C1 GLO GERM UV Off | Background Flash Off |
|---|---|---|---|---|---|
| Pixel Intensity at max frequency | 255 | 158 | 189 | 147 | 146 |
| Normalized Pixel Frequency at max Intensity | 0.639 | 0.025 | 0.031 | 0.029 | 0.042 |

TABLE 8

Example 3 (FIG. 14) and Comparative Example C1 (FIG. 15) on Test Surface #4 (Wood)

| Parameter | Ex. 3 Flash On | Ex. 3 Flash Off | Ex. C1 GLO GERM UV On | Ex. C1 GLO GERM UV Off | Background Flash Off |
|---|---|---|---|---|---|
| Pixel Intensity at max frequency | 256 | 102 | 218 | 63 | 59 |
| Normalized Pixel Frequency at max Intensity | 0.424 | 0.031 | 0.030 | 0.031 | 0.085 |

TABLE 9

Comparative Example C2 (FIG. 16) on Test Surface #4 (Wood)

| Parameter | Ex. C2 DAZO UV On | Ex. C2 DAZO UV Off | Background Flash Off |
|---|---|---|---|
| Pixel Intensity at max frequency | 184 | 56 | 59 |
| Normalized Pixel Frequency at max Intensity | 0.035 | 0.120 | 0.085 |

Curve Fitting Analysis

In order to compare and contrast the response function of surface marking systems employing retroreflective microspheres with those based on UV dyes or microparticles, the pixel intensity histograms shown in FIGS. 4-16 were analyzed by fitting each data set to a best-fitting peak function. This was accomplished automatically using the software program available under the trade designation TABLE-CURVE 2D from Systat Software. The software program was applied to each data set to find the best fitting peak function, from the software's built-in library. The library of peak functions that were selected was constrained to those that had a continuous first derivative. After the curve fit of each data set three useful parameters were available: $L_{MAX}$, $L_{FWHM}$, and $f_{Area}@L_{MAX}$. $L_{MAX}$ is in the range from 0 (black) to 256 (white) and is the pixel intensity or "lightness" at the maximum normalized pixel frequency for the fit function. Conceptually, this $L_{MAX}$ is the same as the Pixel Intensity at max frequency, described above and reported in Tables 4-16. However, the $L_{MAX}$ for a curve fit is based on the applied curve function and will not always be equivalent to the raw data value for Pixel Intensity at max frequency. The value $f_{Area}@L_{MAX}$ is the normalized pixel frequency value corresponding to $L_{MAX}$. $L_{FWHM}$ is in the range from 0 (black) to 256 (white) and is the pixel intensity full width at a normalized pixel frequency value that is exactly half of $f_{Area}@L_{MAX}$.

Figure 17:
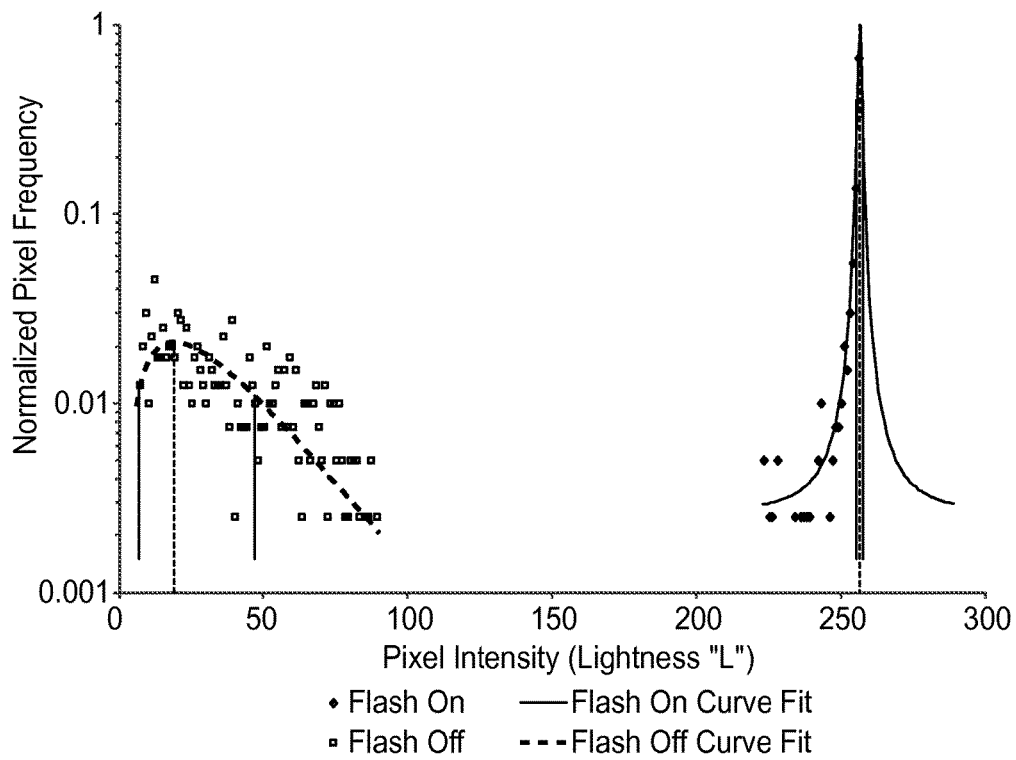
Figure 18:
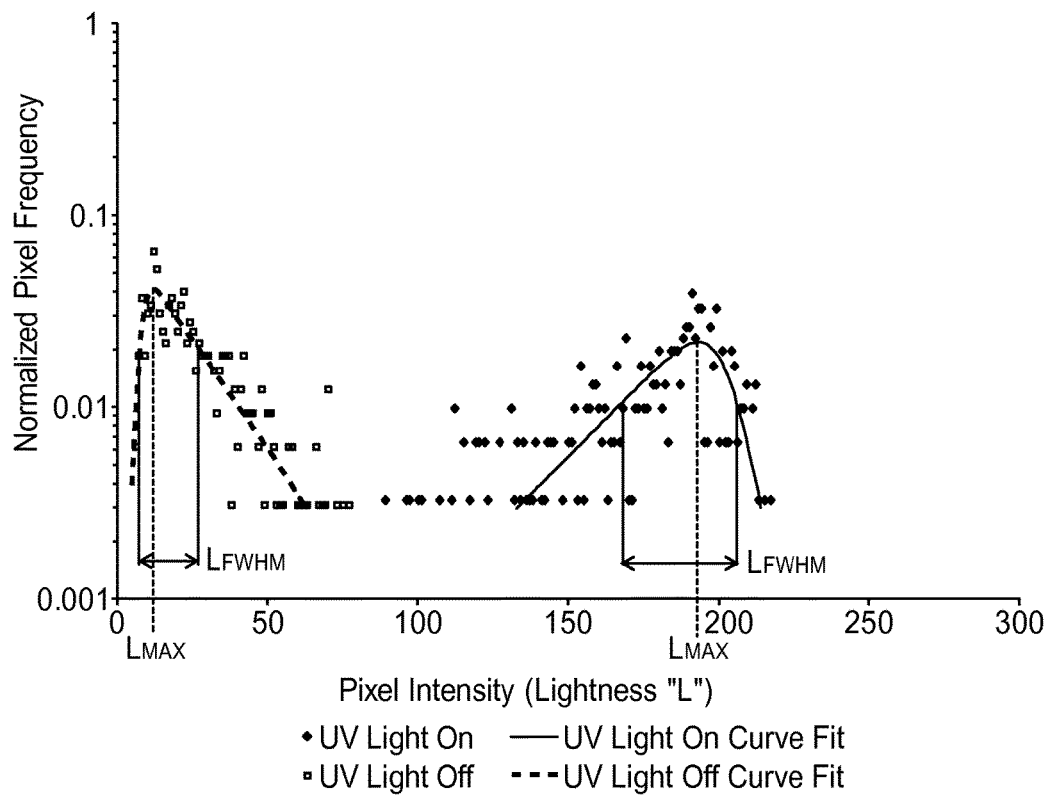

FIGS. 17 and 18 graphically illustrate the curve fitting process applied to the data sets and the results obtained. FIG. 17 uses the data set also presented in FIG. 7 for the Flash On and Flash Off data of Example 3 on Test Surface #1 (black). FIG. 18 uses the data set also presented in FIG. 8 for UV Light On and UV Light Off data of Comparative Example 1 on Test Surface #1 (black). FIGS. 17 and 18 graphically show the curve fit lines, as well as vertical lines which identify $L_{MAX}$ and $L_{FWHM}$.

Additional Analysis

It was not possible to assign a curve function for the non-illuminated Example 2 on Test Surface #1 (black) using the curve fitting software program. It can be seen in FIG. 6 that the data set showed no apparent curve distribution. Without this fit it was not possible to generate a $L_{FWHM}$ value for the non-illuminated Example 2. Although no curve function could be assigned to Example 2 using the software program, the following reasonable estimate was applied. It was visually observed and confirmed by FIGS. 4-7 that Example 2 performed in similar manner to the other visible light, non-UV, particle- or bead-based samples (Example 1, Example 3, and Comparative Example 3) when not illuminated, on Test Surface #1. Therefore, the $L_{FWHM}$ value for Example 2 was estimated as an average of the $L_{FWHM}$ values for Example 1, Example 3, and Comparative Example 3, not illuminated. This provided an estimated $L_{FWHM}$ value of ((47.3+44.0+65.9)/3)=52.4 for Example 2, when not illuminated.

Quality Factor Q

Given these parameters, a relative quality factor Q was also calculated: $Q=L_{MAX}/L_{FWHM}$. Quality factors for both the non-illuminated state of the system, $Q_{Off}$ as well as for the illuminated state of the system, $Q_{On}$ were calculated. As described above, the Q factors described the distribution of pixel intensity across the entirety of the surface mark. High Q factors were representative of surface marks where there is a significant majority of pixels within a very narrow distribution (small $L_{FWHM}$) about a relatively high center intensity (large $L_{MAX}$) and are indicative of a surface marking systems which are easy to see with the naked eye because they are very bright. Low Q factors were representative of the opposite condition: surface marks where the significant majority of pixels have intensities spread out over a broad distribution (large $L_{FWHM}$) centered about a relatively low intensity (small $L_{MAX}$) and are indicative of a surface marking systems which are less easy to see with the naked eye because they are less bright.

Figure 9:
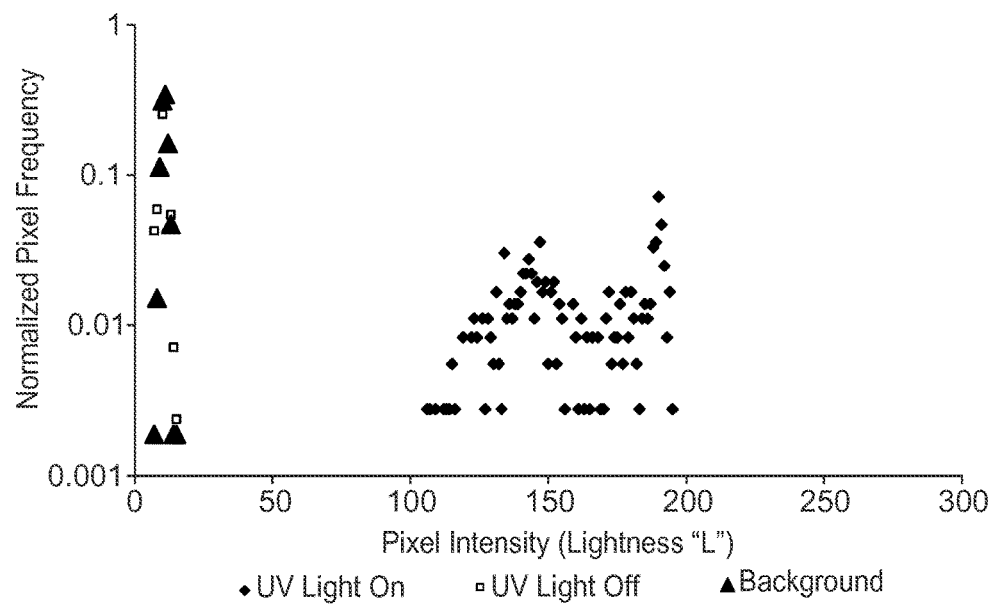
Figure 10:
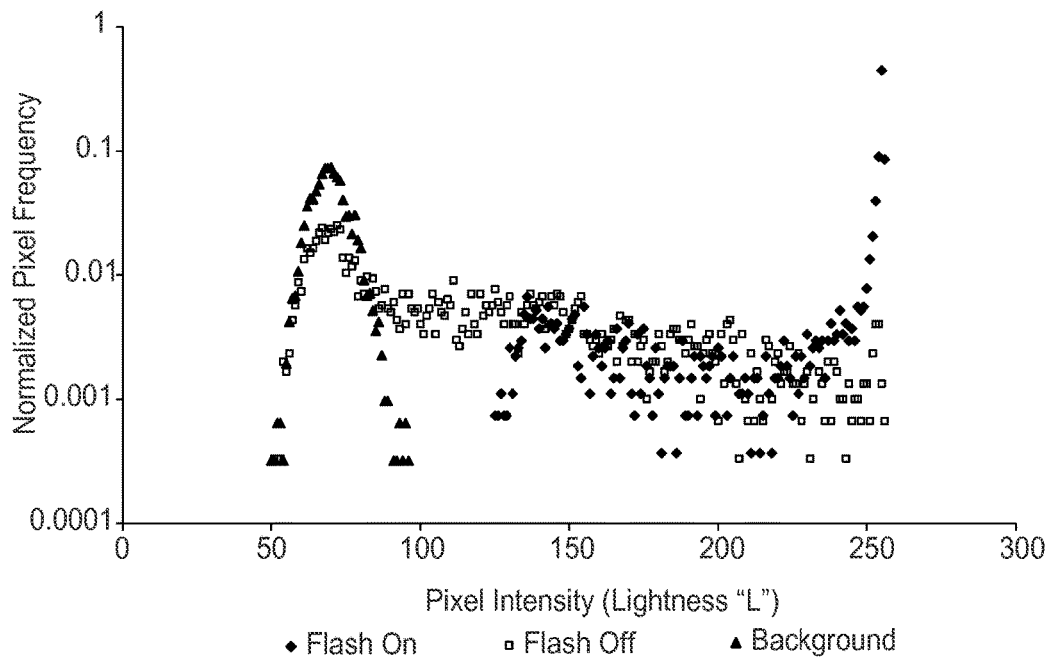
Figure 11:
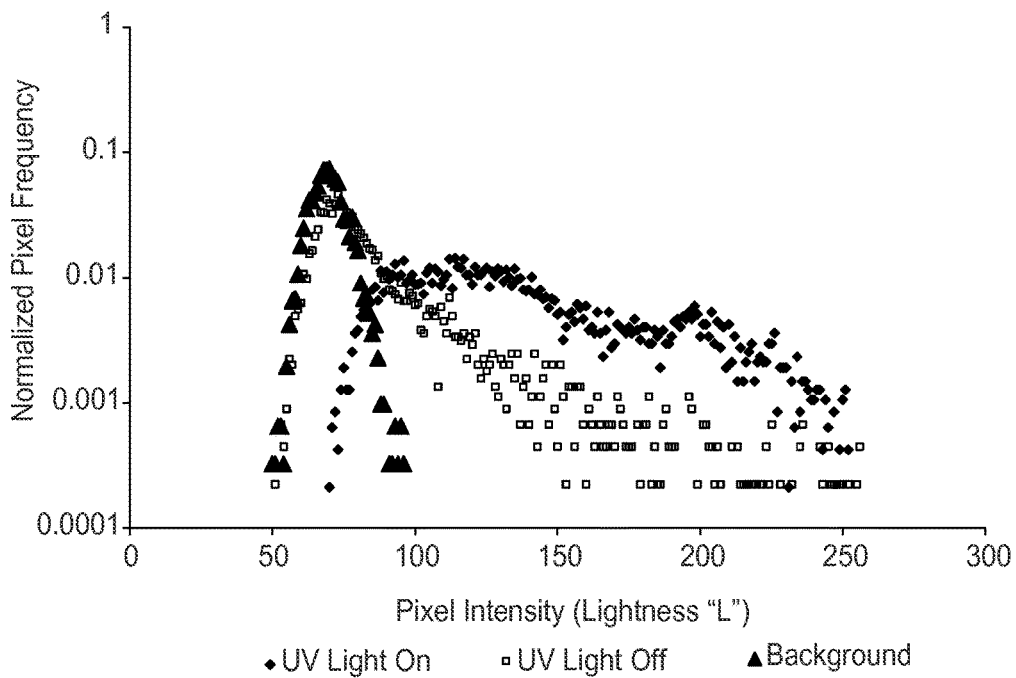
Figure 12:
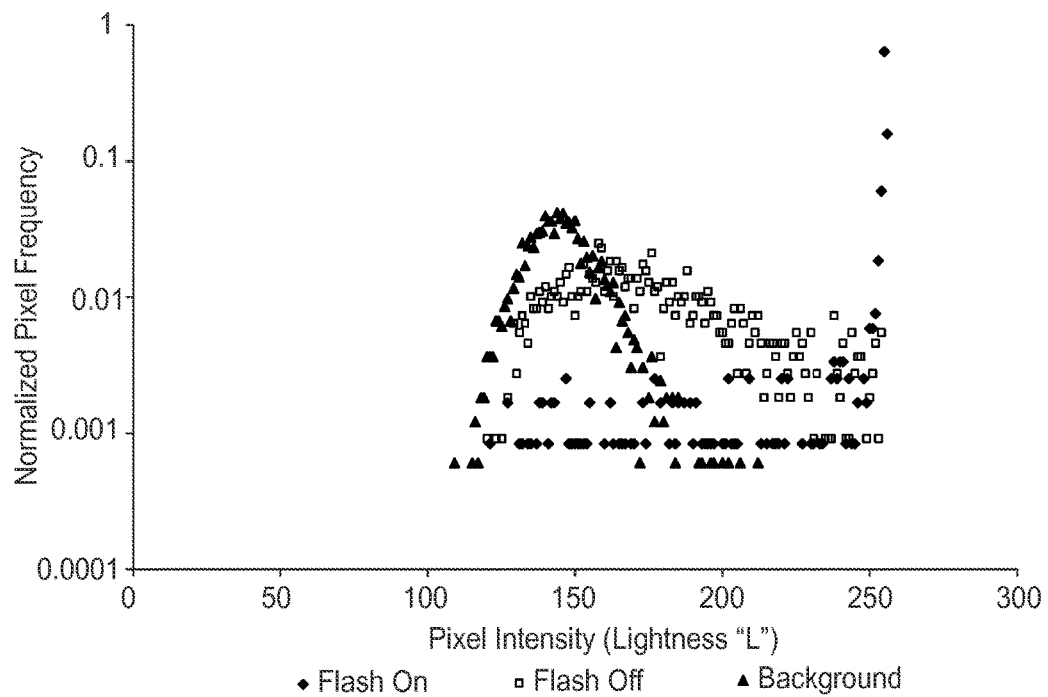
Figure 13:
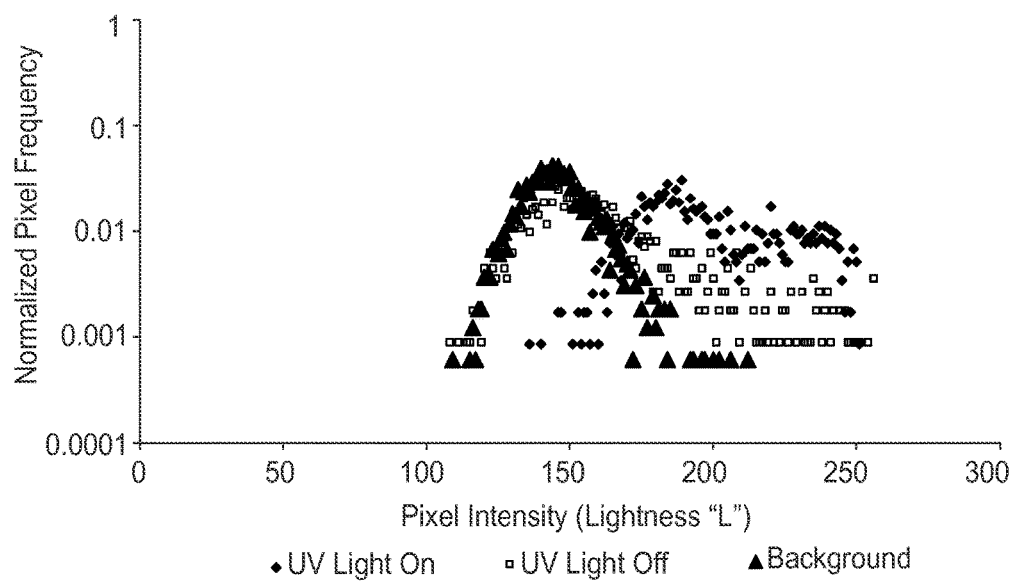
Figure 14:
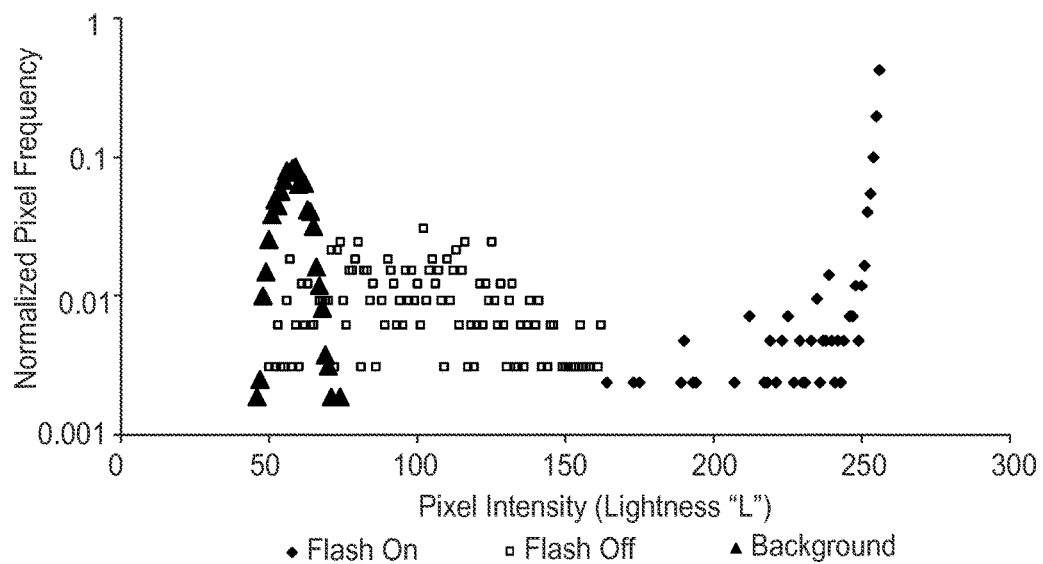
Figure 15:
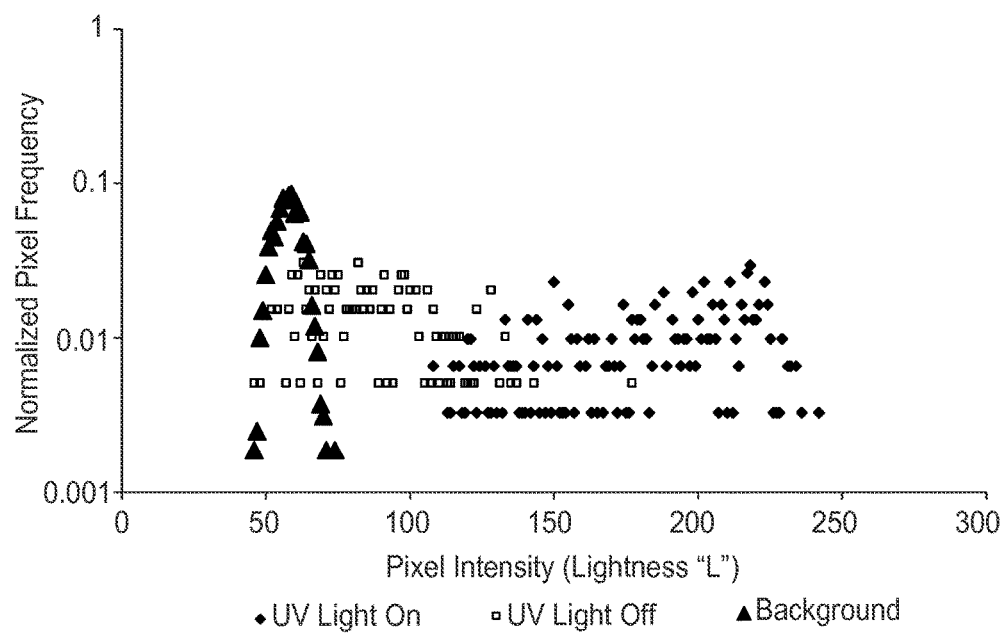
Figure 16:
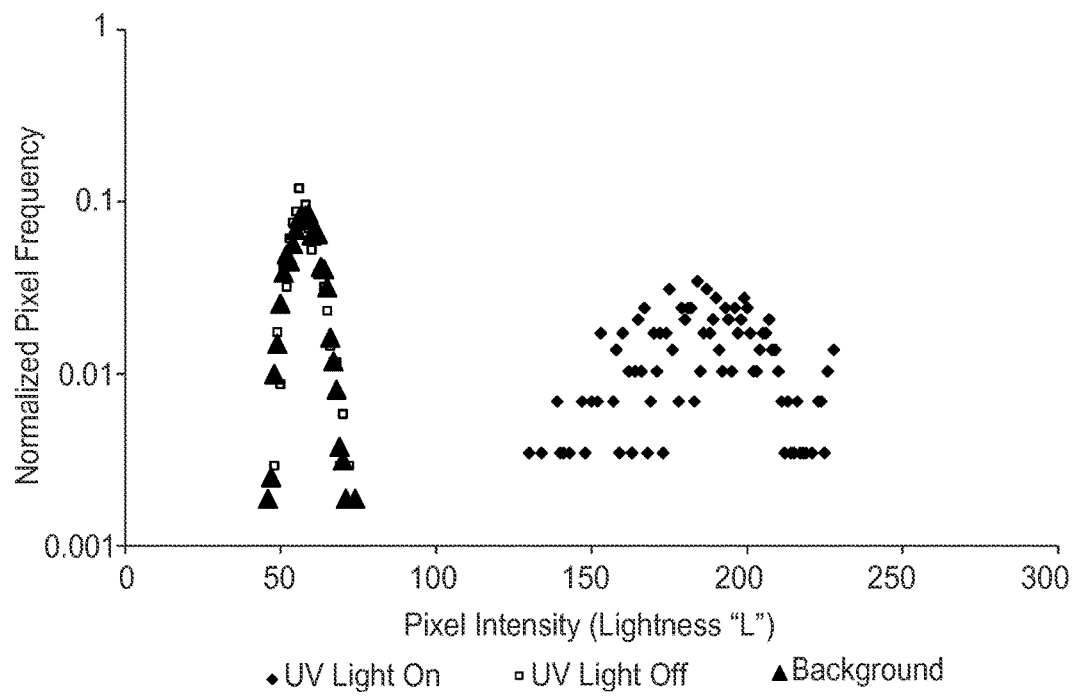

When Comparative Example 2 (DAZO) was illuminated by UV light on Test Surface #1 (black) the distribution of pixel intensity exhibited an apparent bimodal (two peaks) shape, see FIG. 9. In an effort to not force the curve fit towards one peak (at 144.6) or the other peak (at 189.9), the following averaging procedure was applied. The Quality Factor for Comparative Example 2 (DAZO) was illuminated by UV light on Test Surface #1 (black) was the area weighted average of the individual quality factors for each peak: Quality Factor=(Fractional Area of First Peak*Quality Factor of First Peak)+(Fractional Area of Second Peak*Quality Factor of Second Peak)=(0.7*7.5)+(0.3*46.3)=19.2.

TABLE 10

Curve Fit Results for Background (Unmarked Surfaces)

| Example | Test Surface | fArea @ LMAX | LMAX | LFWHM | Quality Factor (LMAX/ LFWHM) |
|---|---|---|---|---|---|
| Ex. 1 | #1 Black | 0.368 | 10.6 | 2.5 | 4.2 |
| Ex. 2 | #1 Black | 0.368 | 10.6 | 2.5 | 4.2 |
| Ex. 3 | #1 Black | 0.368 | 10.6 | 2.5 | 4.2 |
| Ex. 3 | #2 Dark Gray | 0.072 | 69.0 | 12.3 | 5.6 |
| Ex. 3 | #3 Light Gray | 0.038 | 143.4 | 23.4 | 6.1 |
| Ex. 3 | #4 Wood | 0.081 | 57.9 | 12.0 | 4.8 |
| Ex. C1 | #1 Black | 0.368 | 10.6 | 2.5 | 4.2 |
| Ex. C1 | #2 Dark Gray | 0.072 | 69.0 | 12.3 | 5.6 |
| Ex. C1 | #3 Light Gray | 0.038 | 143.4 | 23.4 | 6.1 |
| Ex. C1 | #4 Wood | 0.081 | 57.9 | 12.0 | 4.8 |
| Ex. C2 | #1 Black | 0.368 | 10.6 | 2.5 | 4.2 |
| Ex. C2 | #4 Wood | 0.081 | 57.9 | 12.0 | 4.8 |
| Ex. C3 | #1 Black | 0.368 | 10.6 | 2.5 | 4.2 |

TABLE 11

Curve Fit Results for Non-Illuminated Marking Systems

| Example | Test Surface | fArea @ LMAX | LMAX | LFWHM | Quality Factor (LMAX/ LFWHM) |
|---|---|---|---|---|---|
| Ex. 1 | #1 Black | 0.021 | 35.3 | 44.0 | 0.8 |
| Ex. 2 | #1 Black | 0.011 | 64.8 | 52.4 * | 1.2 |
| Ex. 3 | #1 Black | 0.026 | 19.8 | 65.9 | 0.3 |
| Ex. 3 | #2 Dark Gray | 0.022 | 65.8 | 19.7 | 3.3 |
| Ex. 3 | #3 Light Gray | 0.015 | 158.8 | 61.0 | 2.6 |
| Ex. 3 | #4 Wood | 0.013 | 96.8 | 74.8 | 1.3 |

TABLE 11-continued

Curve Fit Results for Non-Illuminated Marking Systems

| Example | Test Surface | fArea @ LMAX | LMAX | LFWHM | Quality Factor (LMAX/LFWHM) |
|---|---|---|---|---|---|
| Ex. C1 | #1 Black | 0.041 | 12.0 | 18.9 | 0.6 |
| Ex. C1 | #2 Dark Gray | 0.040 | 70.9 | 17.3 | 4.1 |
| Ex. C1 | #3 Light Gray | 0.023 | 146.7 | 35.1 | 4.2 |
| Ex. C1 | #4 Wood | 0.019 | 74.4 | 50.2 | 1.5 |
| Ex. C2 | #1 Black | 0.322 | 10.8 | 2.6 | 4.1 |
| Ex. C2 | #4 Wood | 0.101 | 56.2 | 8.6 | 6.5 |
| Ex. C3 | #1 Black | 0.020 | 39.7 | 47.3 | 0.8 |

* Average of all reflective bead systems (Ex. 1, Ex. 3, Ex. C1) on black surface.

TABLE 12

Curve Fit Results for Illuminated Marking Systems

| Example | Test Surface | fArea @ LMAX | LMAX | LFWHM | Quality Factor (LMAX/LFWHM) |
|---|---|---|---|---|---|
| Ex. 1 | #1 Black | 0.664 | 256.0 | 2.3 | 111.3 |
| Ex. 2 | #1 Black | 1.172 | 255.8 | 0.6 | 412.6 |
| Ex. 3 | #1 Black | 0.667 | 256.0 | 1.8 | 139.9 |
| Ex. 3 | #2 Dark Gray | 0.447 | 255.0 | 1.0 | 255.0 |
| Ex. 3 | #3 Light Gray | 1.137 | 255.3 | 1.0 | 255.3 |
| Ex. 3 | #4 Wood | 0.424 | 256.0 | 2.8 | 91.4 |
| Ex. C1 | #1 Black | 0.023 | 192.9 | 33.6 | 5.7 |
| Ex. C1 | #2 Dark Gray | 0.012 | 105.5 | 76.1 | 1.4 |
| Ex. C1 | #3 Light Gray | 0.022 | 182.5 | 32.0 | 5.7 |
| Ex. C1 | #4 Wood | 0.014 | 217.6 | 67.5 | 3.2 |
| Ex. C2 | #1 Black (1st peak) | 0.022 | 144.6 | 19.3 | 19.2* |
| Ex. C2 | #1 Black (2nd peak) | 0.059 | 189.9 | 4.1 | |
| Ex. C2 | #4 Wood | 0.021 | 191.0 | 45.4 | 4.2 |
| Ex. C3 | #1 Black | 0.011 | 121.1 | 96.3 | 1.3 |

*Average of two curve functions as described above.

Quality Factor Gain Ratio (QFGR=$Q_{On}/Q_{Off}$)

The ratio of $Q_{On}$ to $Q_{Off}$ was calculated for each data set of marker system on a test surface. This ratio of $Q_{On}/Q_{Off}$ was called the Quality Factor Gain Ratio (QFGR) and was used to represent the intensity gain for the system when it transitioned from the non-illuminated to the illuminated state. This gain describes the magnitude by which the surface mark becomes visually apparent to an observer when the illuminating source (visible light or UV) is projected onto the marking system.

Transparancy Ratio

The ratio of $Q_{Off}$ to $Q_{Background}$ was calculated for each data set of marker system on a test surface and is representative of the visual transparency of the surface mark on a given surface. The Q factor determined for the non-marked and non-illuminated surface is $Q_{Background}$. This Transparency Ratio of $Q_{Off}/Q_{Background}$ is indicative of how "covert" the marked surface is to a given observer. Approaching a transparency ratio of 1.0 maximizes the covertness of the system.

TABLE 13

Quality Factor Gain Ratios and Transparency Ratios

| Example | Test Surface | Quality Factor Gain Ratio QON/QOFF | Transparency Ratio QOFF/QBkgd |
|---|---|---|---|
| Ex. 1 | #1 Black | 138.6 | 0.19 |
| Ex. 2 | #1 Black | 333.4 | 0.30 |
| Ex. 3 | #1 Black | 466.3 | 0.07 |
| Ex. 3 | #2 Dark Gray | 76.3 | 0.60 |
| Ex. 3 | #3 Light Gray | 98.0 | 0.42 |
| Ex. 3 | #4 Wood | 70.6 | 0.27 |
| Ex. C1 | #1 Black | 9.0 | 0.15 |
| Ex. C1 | #2 Dark Gray | 0.3 | 0.73 |
| Ex. C1 | #3 Light Gray | 1.4 | 0.68 |
| Ex. C1 | #4 Wood | 2.2 | 0.31 |
| Ex. C2 | #1 Black | 4.6 | 0.99 |
| Ex. C2 | #4 Wood | 0.6 | 1.36 |
| Ex. C3 | #1 Black | 1.5 | 0.20 |

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. A method for determining the cleanliness of a surface, the method comprising:
   providing a surface marking system comprising a plurality of retroreflective microspheres dispersed in or dispensed on a carrier;
   applying the surface marking system to at least one discrete site on the surface;
   illuminating the at least one discrete site on the surface with a visible light source, after a cleaning; and
   detecting retroreflection emitted from the at least one discrete site on the surface in response to illuminating the at least one discrete site to determine the effectiveness of the cleaning of the surface.

2. The method of claim 1, wherein detecting includes visually detecting.

3. The method of claim 1, wherein the surface is an environmental surface.

4. The method of claim 1, wherein the at least one discrete site on the surface is unknown to environmental services staff.

5. The method of claim 1, wherein the surface marking system is covert.

6. The method of claim 1, wherein the plurality of retroreflective beads are randomly distributed in or on the carrier.

7. The method of claim 1, wherein applying the surface marking system includes foaming.

8. The method of claim 1, wherein applying the surface marking system includes dry transfer.

9. The method of claim 1, wherein applying the surface marking system includes contact application.

10. The method of claim 1, wherein applying the surface marking system includes liquid deposition.

11. The method of claim 1, wherein the plurality of retroreflective microspheres are dispersed in the carrier to a concentration of no greater than about $1 \times 10^6$ microspheres/mL of the carrier.

12. The method of claim 1, wherein the plurality of retroreflective microspheres includes an average diameter of 10 to 100 micrometers.

13. The method of claim 1, wherein the carrier includes at least one of a surfactant, a polymeric binder, an adhesive layer, and a combination thereof.

14. A system comprising:
- a surface marking system comprising a plurality of retroreflective microspheres dispersed in or dispensed on a carrier, the surface marking system configured to be applied to at least one discrete site on a surface;
- a visible light source configured to illuminate the at least one discrete site on the surface, after a cleaning; and
- a detection device configured to detect retroreflection emitted from the at least one discrete site on the surface, while being illuminated by the visible light source, to determine the effectiveness of the cleaning of the surface.

15. The method of claim 1, wherein the visible light source includes at least one of a flashlight, a lamp, a lantern, a camera, a smart phone, a smart phone camera, a tablet computer, a tablet computer camera, other portable devices with integrated flash cameras, and a combination thereof.

16. The system of claim 14, wherein the visible light source includes at least one of a flashlight, a lamp, a lantern, a camera, a smart phone, a smart phone camera, a tablet computer, a tablet computer camera, other portable devices with integrated flash cameras, and a combination thereof.

17. The system of claim 14, wherein the detection device includes a camera.

\* \* \* \* \*